United States Patent
Yang et al.

(10) Patent No.: US 9,696,317 B2
(45) Date of Patent: Jul. 4, 2017

(54) GREENER PROCESS TO SYNTHESIZE WATER-SOLUBLE $MN^{2+}$-DOPED CDSSE(ZNS) CORE(SHELL) NANOCRYSTALS FOR RATIOMETRIC TEMPERATURE SENSING, NANOCRYSTALS, AND METHODS IMPLEMENTING NANOCRYSTALS

(71) Applicant: The Trustees of Princeton University, Princeton, NJ (US)

(72) Inventors: Haw Yang, Princeton Junction, NJ (US); Chih-Hao Hsia, Plainsboro, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 304 days.

(21) Appl. No.: 14/352,610

(22) PCT Filed: Oct. 18, 2012

(86) PCT No.: PCT/US2012/060838
§ 371 (c)(1),
(2) Date: Apr. 17, 2014

(87) PCT Pub. No.: WO2013/066630
PCT Pub. Date: May 10, 2013

(65) Prior Publication Data
US 2014/0242631 A1 Aug. 28, 2014

Related U.S. Application Data

(60) Provisional application No. 61/548,486, filed on Oct. 18, 2011.

(51) Int. Cl.
*B82B 3/00* (2006.01)
*G01N 33/58* (2006.01)
(Continued)

(52) U.S. Cl.
CPC ............ *G01N 33/588* (2013.01); *B82Y 30/00* (2013.01); *C01B 19/002* (2013.01); *C09K 11/02* (2013.01);
(Continued)

(58) Field of Classification Search
CPC ..... C09K 11/574; C09K 11/57; C09K 11/584; C09K 11/582; B82Y 30/00; Y10T 428/2991
See application file for complete search history.

(56) References Cited

U.S. PATENT DOCUMENTS 6,872,249 B2   3/2005   Peng et al.
7,250,082 B2   7/2007   Jang et al.
(Continued)

OTHER PUBLICATIONS

Breus et al, "Zwitterionic Biocompatible Quantum Dots for Wide pH Stability and Weak Nonspecific Binding to Cells", ACSNaNo, vol. 3, No. 9, 2009, pp. 2573-2580.*
(Continued)

*Primary Examiner* — Carol M Koslow
(74) *Attorney, Agent, or Firm* — Volpe and Koenig, P.C.

(57) ABSTRACT

Novel $Mn^{2+}$-doped quantum dots are provided. These $Mn^{2+}$-doped quantum dots exhibit excellent temperature sensitivity in both organic solvents and water-based solutions. Methods of preparing the $Mn^{2+}$-doped quantum dots are provided. The $Mn^{2+}$-doped quantum dots may be prepared via a stepwise procedure using air-stable and inexpensive chemicals. The use of air-stable chemicals can significantly reduce the cost of synthesis, chemical storage, and the risk associated with handling flammable chemicals. Methods of temperature sensing using $Mn^{2+}$-doped quantum dots are provided. The stepwise procedure provides the ability to tune the temperature-sensing properties to satisfy specific needs for temperature sensing applications. Water solubility may be achieved by passivating the $Mn^{2+}$-doped quantum
(Continued)

dots, allowing the Mn²⁺-doped quantum dots to probe the fluctuations of local temperature in biological environments.

17 Claims, 9 Drawing Sheets

(51) Int. Cl.
 C09K 11/02 (2006.01)
 C09K 11/56 (2006.01)
 C09K 11/88 (2006.01)
 B82Y 30/00 (2011.01)
 H01L 33/06 (2010.01)
 C01B 19/00 (2006.01)
 G01N 21/64 (2006.01)

(52) U.S. Cl.
 CPC .......... $C09K\ 11/562$ (2013.01); $C09K\ 11/565$ (2013.01); $C09K\ 11/883$ (2013.01); $H01L\ 33/06$ (2013.01); $C01P\ 2002/89$ (2013.01); $C01P\ 2004/04$ (2013.01); $C01P\ 2004/64$ (2013.01); $G01N\ 21/6408$ (2013.01); $Y10T\ 428/2991$ (2015.01)

(56) References Cited

U.S. PATENT DOCUMENTS

| | | | |
|---|---|---|---|
| 7,687,800 B1* | 3/2010 | Kar | B82Y 10/00 257/14 |
| 7,767,260 B2* | 8/2010 | Peng | B82Y 15/00 427/212 |
| 7,919,012 B2 | 4/2011 | Peng et al. | |
| 2003/0030067 A1 | 2/2003 | Chen | |
| 2003/0148544 A1* | 8/2003 | Nie | B82Y 15/00 436/524 |
| 2007/0111324 A1 | 5/2007 | Nie et al. | |
| 2007/0269382 A1* | 11/2007 | Santra | A61K 49/0002 424/9.323 |
| 2010/0055462 A1 | 3/2010 | Cao | |
| 2010/0123155 A1 | 5/2010 | Pickett et al. | |
| 2011/0014473 A1 | 1/2011 | Ying et al. | |
| 2011/0108799 A1 | 5/2011 | Pickett et al. | |
| 2011/0223110 A1 | 9/2011 | Bartel et al. | |

OTHER PUBLICATIONS

Price et al., "Nanocrystalline gold arylthiolate molecules," http://smartech.gatech.edu/jspui/bitstream/1853/14051/1/price_ryan_c_200612_phd.pdf> (2006) 1-140.
Bera et al., "Quantum Dots and Their Multimodal Applications: A Review," Materials (2010) 3:2260-2345.
Breus, V. V. et al., "Zwitterionic Biocompatible Quantum Dots for Wide pH Stability and Weak Nonspecific Binding to Cells", ACS Nano, 2009, vol. 3, pp. 2573-2580.
Evans, C. M. et al., "Mysteries of TOPSe Revealed: Insights Into Quantum Dot Nucleation", J. Am. Chem. Soc., 2010, vol. 132, pp. 10973-10975.
Han, M. et al., "Quantum-Dot-Tagged Microbeads for Multiplexed Optical Coding of Biomolecules", Nature Biotech., 2001, vol. 19, pp. 631.
Jang, E. et al., "High Quality CdSeS Nanocrystals Synthesized by Facile Single Injection Process and Their Electroluminescence", Chem. Comm., 2003, p. 2964.
Jasieniak, J. et al., "Phosphone-Free Synthesis of CdSe Nanocrystals", J. Phys. Chem. B, 2005, vol. 109, pp. 20665-20668.
Li, J. J. et al., "Large-Scale Synthesis of Nearly Monodisperse CdSe/CdS Core/Shell Nanocrystals Using Air-Stable Reagents via Successive Ion Layer Adsorption and Reaction", J. Am. Chem. Soc., 2003, vol. 125, pp. 12567-12575.

Moloney, M. P. et al., "Chiral Highly Luminescent CdS Quantum Dots", Chem. Commun., 2007, pp. 3900-3902.
Ouyang, J. et al., "Noninjection, One-Pot Synthesis of Photoluminescent Colloidal Homogeneously Alloyed CdSeS Quantum Dots", J. Phys. Chem. C, 2009, vol. 113, pp. 5193-5200.
Peng, Z. A. et al., "Formation of High-Quality CdTe, CdSe, and CdS Nanocrystals Using CdO as Precursor", J. Am. Chem. Soc., 2001, vol. 123, pp. 183-184.
Vlaskin, V. A. et al., "Tunable Dual Emission in Doped Semiconductor Nanocrystals", Nano. Lett., 2010, vol. 10, pp. 3670-3674.
Yang, Y. et al., "Radial-Position-Controlled Doping in CdS/ZnS Core/Shell Nanocrystals", J. Am. Chem. Soc., 2006, vol. 128, pp. 12428-12429.
Yang, Y. et al., "On Doping CdS/ZnS Core/Shell Nanocrystals With Mn", J. Am. Chem. Soc., 2008, vol. 130, pp. 15649-15661.
Zou, Y. et al., "Noninjection Synthesis of CdS and Alloyed CdSxSe1-x Nanocrystals Without Nucleation Initiators,", Nonoscale Res. Lett., 2010, vol. 5, pp. 966-971.
Bailey and Nie, "Alloyed Semiconductor Quantum Dots: Tuning the Optical Properties Without Changing the Particle Size", 2003, J. Am. Chem. Soc., vol. 125, pp. 7100-7106.
Berthou and Jorgensen, "Optical Fiber Temperature Sensor Based on Upconversion-Excited Fluorescence", 1990, Opt. Lett., vol. 15, No. 19, pp. 1100-1102.
Chen et al., "Crystal Field, Phonon Coupling and Emissino Shift of Mn2+ In ZnS:Mn Nanoparticles", 2001, J. Appl. Phys., vol. 89, No. 2, pp. 1120-1129.
Chen et al., "Measurement of Energy Transfer Time in Colloidal Mn-Doped Semiconductor Nanocrystals", 2010, J. Phys. Chem. C, vol. 114, pp. 4418-4423.
Ithurria et al., "Mn2+ as a Radial Pressure Gauge in Colloidal Core/Shell Nanocrystals", 2007, Phys. Rev. Lett., vol. 99, p. 265501.
Kusama et al., "Line Shift Method for Phosphor Temperature Measurements", 1976, Jpn. J. Appl. Phys., vol. 15, No. 12, pp. 2349-2368.
Maestro et al., "CdSe Quantum Dots for Two-Photon Fluorescence Thermal Imaging", 2010, Nano Lett., vol. 10, pp. 5109-5115.
Medintz et al., "Quantum Dot Bioconjugates for Imaging, Labelling and Sensing", 2005, Nat. Mater., vol. 4, pp. 435-446.
Murray et al., "Synthesis and Characterization of Nearly Monodisperse CdE (E=S, Se, Te) Semiconductor Nanocrystallites", 1993, J. Am. Chem. Soc., vol. 115, pp. 8706-8715.
Song et al., 2011, ACS Nano, vol. 128, pp. 13320-13321, "Hole Transfer from Single Quantum Dots".
Susumu et al., "Multifunctional Compact Zwitterionic Ligands for Preparing Robust Biocompatible Semiconductor Quantum Dots and Gold Nanoparticles", 2011, J. Am. Chem. Soc., 2011, vol. 133, pp. 9480-9496.
Wade et al., "Fluorescence Intensity Ratio Technique for Optical Fiber Point Temperature Sensing", 2003, J. Appl. Phys., vol. 94, No. 8, pp. 4743-4756.
Yang et al., "Thermogenesis Detection of Single Living Cells via Quantum Dots", 2010, In the 23rd IEEE Micro Electro Mechanical Systems Conference, Hong Kong, pp. 963-966.
Yang et al., "Quantum Dot Nano Thermometers Reveal Heterogeneous Local Thermogenesis in Living Cells", 2011, ACS Nano, vol. 5, No. 6, pp. 5067-5071.
Ye et al., "Ratiometric Temperature Sensing With Semiconducting Polymer Dots", 2011, J. Am. Chem. Soc., vol. 133, pp. 8146-8149.
Zhong et al., "Composition-Tunable ZnXCd1-XSe Nanocrystals With High Luminescence and Stability", 2003, J. Am. Chem. Soc., vol. 125, pp. 8589-8594.
Hsia et al., "An Accessible Approach to Preparing Water-Soluble Mn2+-Doped CdSSe)ZnS (Core) Shell Nanocrystals for Ratiometric Temperature Sensing", Department of Chemistry, Princeton University, Princeton, New Jersey 08544, 53 Pages.

* cited by examiner

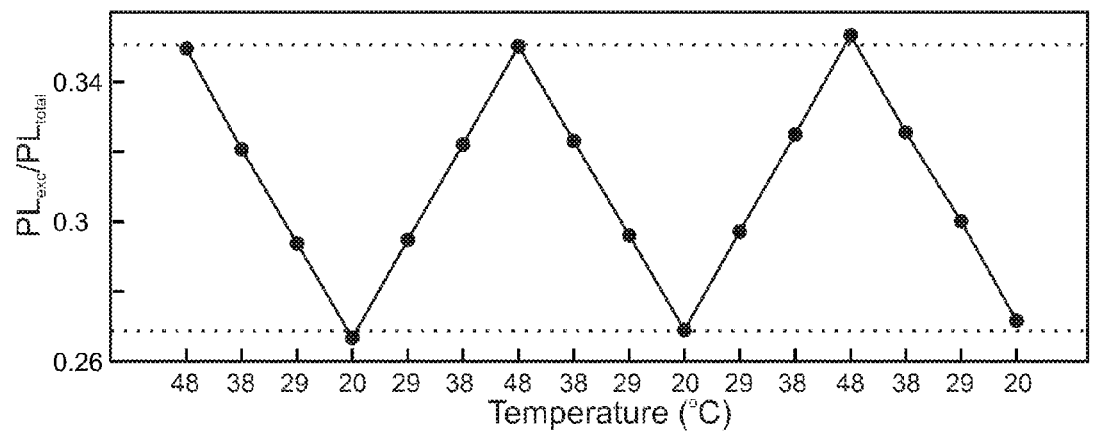
FIG. 6
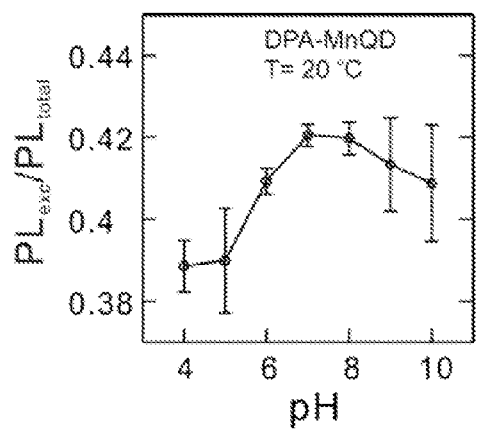 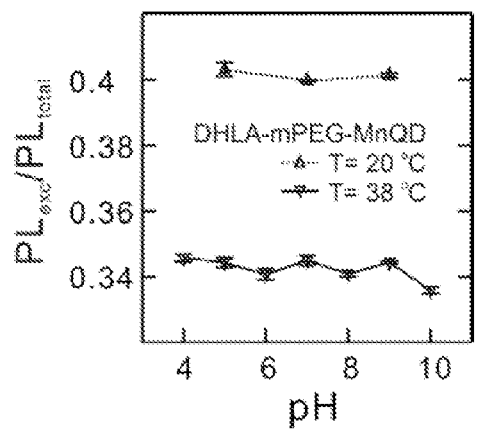
FIG. 7A
FIG. 7B

US 9,696,317 B2

GREENER PROCESS TO SYNTHESIZE WATER-SOLUBLE $MN^{2+}$-DOPED CDSSE(ZNS) CORE(SHELL) NANOCRYSTALS FOR RATIOMETRIC TEMPERATURE SENSING, NANOCRYSTALS, AND METHODS IMPLEMENTING NANOCRYSTALS

This application is a 35 U.S.C. §371 national stage application of PCT/US2012/060838, which was filed Oct. 18, 2012 and claims the benefit of U.S. Provisional Application No. 61/548,486, which was filed Oct. 18, 2011, both of which are incorporated herein by reference as if fully set forth.

This invention was made with government support under Subaward #6915220 from the University of California, Lawrence Berkeley National Laboratory under its Department of Energy Prime Award #DE-AC02-05CH11231. The government has certain rights in this invention.

FIELD OF INVENTION

The disclosure relates to $Mn^{2+}$-doped quantum dots, methods of their synthesis and methods of their utilization.

BACKGROUND

Temperature is a fundamental yet hitherto underappreciated thermodynamic parameter in many environments. In cellular environments temperature may affect reaction kinetics, chemical equilibria, as well as the physical states of nucleic acids and proteins. Quantum dot-based nano thermometers are promising because of their lasting luminescence stability. Previously published ratiometric temperature-sensitive $Mn^{2+}$-doped quantum dots were made by using expensive and air-sensitive chemicals, and their temperature-sensing capability was not demonstrated in water-based solutions. Furthermore, previously published $Mn^{2+}$-doped QDs synthesized with air-stable chemicals did not exhibit ratiometric temperature sensitivity.

Generally, QD nano thermometers rely on temperature-dependent changes in their excitonic emission characteristics, a property that extends to the single-particle level. Typically, at higher temperatures, the excitonic emission exhibits red-shifted frequency and increased non-radiative relaxation rates (shortened excited-state lifetime, also manifested as broadened emission profile and reduced intensity). These temperature-dependent properties have been used to detect the temperature of individual living cells (Yang et al., 2010, In The 23rd IEEE Micro Electro Mechanical Systems Conference, Hong Kong, 963-66; Maestro et al., 2010, Nano Lett., 10, 5109-15, which are incorporated herein by reference as if fully set forth). Using QDs as nano thermometers, Yang et al. recently reported the first experimental evidence of heterogeneous intracellular temperature progression responding to the chemical $Ca^{2+}$ shock and the physical cold shock (rather than the commonly assumed picture that the intracellular temperature is homogeneous under all conditions) (Yang et al., 2011, ACS Nano, 5, 5067-71, which is incorporated herein by reference as if fully set forth). The report also underscores the need for much-improved local temperature reporters because the single-parameter quantum dot temperature sensors (based solely on the emission frequency or intensity, or the excited-state lifetime) are not sufficiently accurate for quantifying the biological and biochemical heat generation. Beyond single-parameter temperature sensing, a ratiometric scheme is expected to be more accurate because it uses two readouts to afford self-calibrated results. Recently, a ratiometric scheme has been shown to report temperature in cellular environments using rare earth-doped structures and semiconducting polymer dots (Ye et al., 2011, J. Am. Chem. Soc., 133, 8146-49, which is incorporated herein by reference as if fully set forth). The first example of using emission intensity ratio (EIR) to sense temperature based on Boltzmann-type distribution was demonstrated in rare earth-doped materials (Kusama et al., 1976, Jpn. J. Appl. Phys., 15, 2349-68, which is incorporated herein by reference as if fully set forth) and subsequently studied extensively within the family of rare earth-doped materials (Berthou and Jorgensen, 1990, Opt. Lett., 15, 1100-02; Wade et al., 2003, J. Appl. Phys., 94, 4743-56, which are incorporated herein by reference as if fully set forth). Recently, Vlaskin et al. extended the EIR technique to sense temperature using $Mn^{2+}$-doped QDs (Vlaskin et al., 2010, Nano Lett., 10, 3670-74, which is incorporated herein by reference as if fully set forth). The $Mn^{2+}$-doped QDs have also been shown to exhibit temperature-sensing capability to show changes within 0.2° C. using the relative intensity between the excitonic and the $Mn^{2+}$ emissions, which are both temperature dependent (Vlaskin et al., 2010, Nano Lett., 10, 3670-74, which is incorporated herein by reference as if fully set forth). The salient properties of the $Mn^{2+}$-doped QDs make them a possible candidate for a much-improved local temperature sensor for intracellular thermometry. However, the temperature-sensing capability of the $Mn^{2+}$-doped QDs has previously only been demonstrated in the bio-incompatible toluene solvent.

SUMMARY

In an aspect, the invention relates to an $Mn^{2+}$-doped quantum dot. The $Mn^{2+}$-doped quantum dot includes a fluorescent semiconductor core; an initial shell covering the fluorescent semiconductor core; an $Mn^{2+}$ dopant associated with the initial shell; and a protection shell covering the initial shell and the $Mn^{2+}$ dopant. The initial shell is an initial ZnS shell, an initial CdS shell, or an initial ZnSe shell. The protection shell is a ZnS protection shell, a ZnSe protection shell, or a $Zn_{1-x}Cd_xS$ protection shell. X is the ratio of Cd/(Cd+Zn) in the $Zn_{1-x}Cd_xS$ protection shell and has a value from 0 to 0.5.

In an aspect, the invention relates to an $Mn^{2+}$ and $Cd^{2+}$ co-doped quantum dot. The $Mn^{2+}$ and $Cd^{2+}$ co-doped quantum dot includes a CdSe core; an initial shell covering the CdSe core; an $Mn^{2+}$ dopant associated with the initial shell; and a $Zn_{1-x}Cd_xS$ protection shell covering the initial shell and the $Mn^{2+}$ dopant. X is the ratio of Cd/(Cd+Zn) in the $Zn_{1-x}Cd_xS$ protection shell and has a value from 0 to 0.5. The initial shell is an initial ZnS shell, an initial CdS shell, or an initial ZnSe shell In an aspect, the invention relates to a method of producing an $Mn^{2+}$-doped quantum dot. The method includes providing a fluorescent semiconductor core; coating the fluorescent semiconductor core with an initial shell to form a coated core; doping the coated core with $Mn^{2+}$ to form an $Mn^{2+}$-doped coated core; and covering the $Mn^{2+}$-doped coated core with a protection shell. The initial shell is an initial ZnS shell, an initial CdS shell, or an initial ZnSe shell. The protection shell is a ZnS protection shell, a ZnSe protection shell, or a $Zn_{1-x}Cd_xS$ protection shell. X is the ratio of Cd/(Cd+Zn) in the $Zn_{1-x}Cd_xS$ protection shell and has a value from 0 to 0.5.

In aspect, the invention relates to a method of producing an $Mn^{2+}$ and $Cd^{2+}$ co-doped quantum dot. The method includes providing a CdSe core; coating the CdSe core with an initial shell to form a coated core; doping the coated core with $Mn^{2+}$ to form an $Mn^{2+}$-doped coated core; and covering the $Mn^{2+}$-doped ZnS coated core with a $Zn_{1-x}Cd_xS$ protection shell. The initial shell is an initial ZnS shell, an initial CdS shell, or an initial ZnSe shell. X is the ratio of Cd/(Cd+Zn) in the $Zn_{1-x}Cd_xS$ protection shell and has a value from 0 to 0.5.

In an aspect, the invention relates to a method of labeling a biological specimen. The method includes contacting the biological specimen with an $Mn^{2+}$-doped quantum dot.

In an aspect, the invention relates to a method of sensing nanoscale temperature fluctuations in a biological material. The method includes contacting the biological material with an $Mn^{2+}$-doped quantum dot; exciting the $Mn^{2+}$-doped quantum; measuring the excitonic emission and $Mn^{2+}$ emission; calculating the emission intensity ratio; and determining the temperature based on the emission intensity ratio.

In an aspect, the invention relates to a method of sensing the local temperature of a nano- or micro-fabricated device. The method includes contacting the nano- or micro-fabricated device with an $Mn^{2+}$-doped quantum dot; exciting the $Mn^{2+}$-doped quantum dot; measuring the excitonic emission and $Mn^{2+}$ emission; calculating the emission intensity ratio; and determining the temperature based on the emission intensity ratio.

In an aspect, the invention relates to a method of sensing temperature in a sample. The method includes contacting the sample with an $Mn^{2+}$-doped quantum dot.

BRIEF DESCRIPTION OF THE DRAWINGS

The following detailed description of the preferred embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings:

FIG. 1A illustrates a synthetic scheme; a method for making a water-soluble $Mn^{2+}$-doped quantum dot (MnQD).

FIG. 6 illustrates temperature-dependent cycles of $PL_{exc}/PL_{total}$ of DPA-Mn17ZnS10 in PBS buffer, depicting the ratiometric fluorescence stability of QDs. The dashed lines serve as guides for the eye.

FIG. 7A illustrates pH-dependent $PL_{exc}/PL_{total}$ of DPA-MnQDs. FIG. 7B illustrates pH-independent $PL_{exc}/PL_{total}$ of DHLA-mPEG-MnQDs.

FIG. 10A illustrates an emission image from calcein AM (indicting live cells). FIG. 10B illustrates an emission image from quantum dots. FIG. 10C illustrates the overlaid image of FIGS. 10A and 10B. Calcein AM is illustrated in grey and quantum dots are illustrated in black.

DETAILED DESCRIPTION OF THE PREFERRED EMBODIMENTS

Figure 1B:
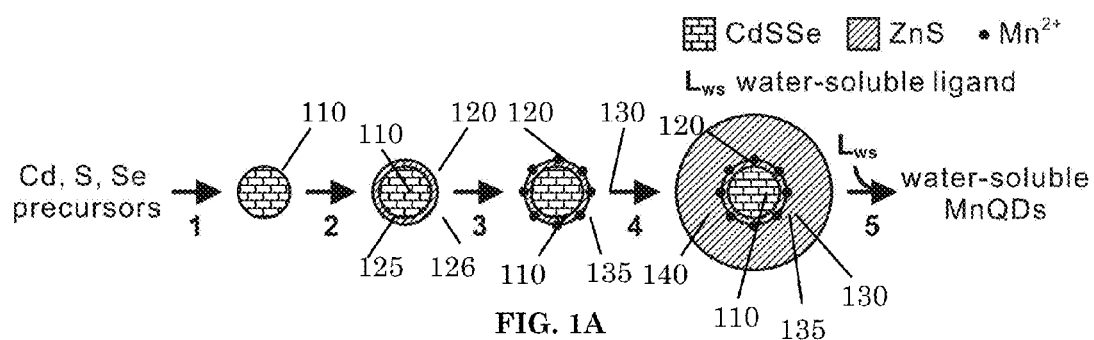
FIG. 1B illustrates the chemical structures of diphenylphosphine selenide (DPPSe), a Se precursor for CdSSe core synthesis, and D-penicillamine (DPA).
Figure 1B:
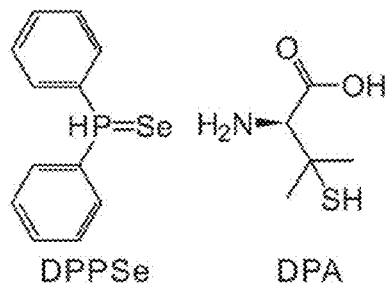
Figure 1C:
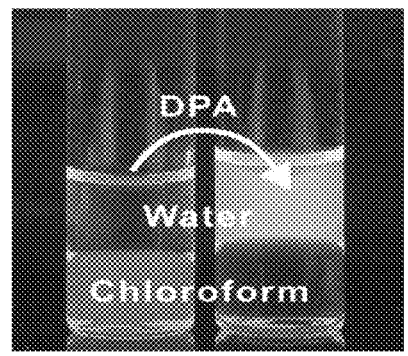
FIG. 1C illustrates a photograph of MnQDs in chloroform contrasting that of DPA coated $Mn^{2+}$-doped quantum dots (DPA-MnQDs) in water.

Certain terminology is used in the following description for convenience only and is not limiting. The words "a" and "one," as used in the claims and in the corresponding portions of the specification, are defined as including one or more of the referenced item unless specifically stated otherwise. The phrase "at least one" followed by a list of two or more items, such as "A, B, or C," means any individual one of A, B or C as well as any combination thereof.

As used herein, the terms "nanocrystal" and "quantum dot" are interchangeable as are the terms "nanocrystals" and "quantum dots." These terms refer to the quantum dots made by the methods herein or otherwise disclosed herein. As used herein, the term "MnQD" refers to an $Mn^{2+}$-doped quantum dot. An $Mn^{2+}$-doped quantum dot may include only $Mn^{2+}$ as a dopant. An $Mn^{2+}$ doped quantum dot may include $Mn^{2+}$ as a dopant and one or more other dopant. An $Mn^{2+}$-doped quantum dot may be an $Mn^{2+}$ and $Cd^{2+}$ co-doped quantum dot.

A new synthetic scheme allowing structural modifications to temperature-sensitive and water soluble D-penicillamine-passivated $Mn^{2+}$-doped (CdSSe)ZnS (core)shell nanocrystals (MnQDs) using air-stable chemicals is contained herein. The temperature-dependent optical properties of the nanocrystals were tuned by changing their structure and composition—the ZnS shell thickness and the $Mn^{2+}$-dopant concentration. Thick ZnS shells significantly reduce the interference of nonradiative transitions on ratiometric emission intensities. High dopant concentration affords consistent temperature sensitivity. The results herein underscore the generalizability of an emission intensity ratio scheme for temperature sensing. Embodiments herein include methods of making MnQDs, new MnQDs and compositions including MnQDs, methods of labeling with MnQDs, and methods of MnQD ratiometric temperature sensing. The temperature sensing may be via flexible, glove box-free routes.

A new approach to preparing ratiometric temperature-sensing MnQDs with a previously unreported base structure of (CdSSe)ZnS (core)shell, where the $Mn^{2+}$ dopant resides in the shell, is reported herein. These MnQDs have completely different chemical structures but share features of true temperature sensing mechanism with the quantum dots made by Vlaskin et al., 2010, Nano Lett., 10, 3670-74, which is incorporated herein by reference as if fully set forth. The structure as well as the synthetic procedure were chosen and developed to be approachable to researchers without access to specialized synthesis instrumentation. A broad range of scientists, including physical biologists and biophysicists, may want to use intracellular temperature sensors as one of their investigative tools. Therefore, while the functionality of these new nano thermometers was the primary concern, special attention was paid to their accessibility, i.e., using air-stable chemicals and general procedures that may not require expensive and specialized equipment, such as a glovebox. The use of air-stable chemicals renders this procedure as an effort to become "greener"—the cost of synthesis equipment and chemical storage and the risk associated with handling highly flammable chemicals commonly used in the synthesis of quantum dots may be significantly decreased. ZnS was used as the chief shell composition because it allowed capitalization on the relatively more mature development of quantum dot passivation with hydrophilic ligands (Susumu et al., 2011, J. Am. Chem. Soc., 2011, 133, 9480-96; Breus et al., 2009, ACS Nano, 3, 2573-80; Medintz et al., 2005, Nat. Mater., 4, 435-46, which are incorporated herein by reference as if fully set forth). This procedure also allowed variation in the MnQD structure at different points of the step-wise scheme to tune its temperature-sensing properties for optical readouts. To this end, two examples of tuning ratiometric temperature-sensing behavior by varying the thickness of the ZnS shell and the $Mn^{2+}$ dopant concentration are shown.

An embodiment provides a method of producing an MnQD. Referring to FIG. 1A, the method may include providing a fluorescent semiconductor core 110, coating the core with an initial ZnS shell 120 to form a ZnS coated core 125, doping the ZnS coated core 125 with $Mn^{2+}$ dopant 130 to form an $Mn^{2+}$-doped ZnS coated core 135, and covering the $Mn^{2+}$-doped ZnS coated core 125 with a ZnS protection shell 140.

The fluorescent semiconductor core 110 may be a CdSSe core, as illustrated in FIG. 1A. A CdSSe core may be prepared by any method. A "Route A" method of CdSSe core preparation may include combining a sulfur-selenium (S—Se) precursor solution and a cadmium (Cd) precursor solution. Combining may include injecting an S—Se precursor solution into a Cd precursor solution, which may be hot. An injecting process includes loading the S—Se precursor solution in a syringe and swiftly adding the S—Se precursor solution into a flask containing the Cd precursor solution via the syringe. An S—Se precursor solution may be prepared using sulfur, diphenylphosphine selenide (DPPSe) and 1-octadecene (ODE). A Cd precursor solution may be prepared using cadmium oxide (CdO), oleic acid and ODE. The method may include maintaining the temperature at, or adjusting the temperature to a crystal formation temperature. The method may include keeping the mixture at the crystal formation temperature for a crystal formation time. The crystal formation temperature may be 265° C. The crystal formation time may be 8 minutes. The method may include quenching crystal formation. Quenching may include lowering the temperature below the crystal formation temperature. The mixture may be cooled to room temperature. The method of CdSSe core preparation may include washing the resultant CdSSe nanocrystals. Washing may include precipitating by adding acetone and centrifuging to form a pellet. The pellet may be resuspended in toluene, and methanol may be added. The resulting mixture may form a turbid solution. The solution may be centrifuged and the precipitate may be resuspended in hexane. The suspension may again be centrifuged, and the supernatant retained. The nanocrystals in the supernatant may be filtered.

A "Route B" method of CdSSe core preparation may include heating cadmium acetate dihydrate, ODE and oleic acid, cooling the resulting solution and adding Se and sulfur. The reaction mixture be then be heated and the nanocrystals allowed to grow. The method may include quenching the reaction by injecting ambient temperature ODE. The method may include removing the heat source and allowing the product to cool to room temperature. The resultant CdSSe nanocrystals may be washed using the same procedure as above.

A method of CdSSe core preparation may include synthesis by a Route A method as described in example 5. A method of CdSSe core preparation may include synthesis by a Route B method as described in example 6.

The fluorescent semiconductor core 110 may include a cadmium-free fluorescent semiconductor core. Non-limiting examples of cadmium-free fluorescent semiconductor cores include copper indium sulfide ($CuInS_2$), zinc indium copper sulfide ((ZnInCu)S) and indium phosphide (InP). $CuInS_2$, (ZnInCu)S and InP may be utilized in cadmium-free fluorescent semiconductor cores; they can be coated with ZnS shell. Using cadmium-free fluorescent semiconductor cores can overcome the consideration of toxicity of cadmium cations. In addition, in vivo temperature sensing can be achieved when using $CuInS_2$ and InP quantum dots as cores, because their emission wavelengths are in the range of near infrared, the so-called optical window in biological tissue.

The $Mn^{2+}$ dopant of any quantum dot or method herein may be referred to as an emissive dopant. In an embodiment, the $Mn^{2+}$ dopant in a quantum dot or method herein may be replaced or supplemented with another emissive dopant. The emissive dopants 130 may include rare-earth ion dopants. Non-limiting examples of rare-earth ion dopants include Praseodymium ($Pr^{3+}$), Neodymium ($Nd^{3+}$), Samarium ($Sm^{3+}$), Europium ($Eu^{3+}$), Erbium ($Er^{3+}$), Dysprosium ($Dy^{3+}$), and Ytterbium ($Yb^{3+}$).

Growing initial shells, adding emissive dopants, and growing protection shells may be accomplished by methods known to the skilled artisan. A non-limiting example of growing an initial shell includes steps of loading the Zn and S precursor solutions in separate syringes and adding the Zn and S precursor solutions alternatively into a flask containing the fluorescent semiconductor core solution via the syringes. A non-limiting example of adding emissive dopants includes steps of loading the emissive dopant precursor solution in a syringe and adding the emissive dopant precursor solution into a flask containing the fluorescent core with an initial ZnS shell via the syringe. A non-limiting example of growing a protection shell includes steps of loading the Zn and S precursor solutions in separate syringes and adding the Zn and S precursor solutions alternatively into a flask containing the fluorescent semiconductor core solution via the syringes.

The method may be adapted to provide an alternate initial shell. The initial shell 120 may be a ZnS initial shell, a CdS initial shell, or a ZnSe initial shell.

The method may be adapted to delete steps of providing an initial shell and instead associate the emissive dopant at the interface of the fluorescent semiconductor core 110 and the protection shell 140.

The method may be adapted to provide an alternate protection shell 140. The protection shell 140 may be a ZnS protection shell, a ZnSe protection shell, or a $Zn_{1-X}Cd_XS$ protection shell, where X is the ratio Cd/(Cd+Zn) and has a value from 0 to 0.5.

The method of producing an $Mn^{2+}$-doped quantum dot may include passivating the quantum dot. Passivating may include sonicating the quantum dot in a suspension containing a passivating agent. Passivating may also be referred to as capping, and a passivating agent may be referred to as a capping agent. Passivating may include performing biphasic exchange and additional sonication. Passivating may include retrieving the quantum dot by collecting the aqueous layer, treating with ethanol and centrifuging the resulting solution. The precipitated quantum dots may be re-dispersed in a buffer solution. The quantum dots may then be annealed for better stability in water-based solvents for photoluminescence and lifetime measurements. Passivating may allow the $Mn^{2+}$-doped quantum dot to probe the fluctuations of local temperature in biological environments. Passivating agents may include but are not limited to D-penicillamine (DPA). Passivating agents may include other compact hydrophilic agents including but not limited to cystine and dihydrolipoic acid.

The method of producing an MnQD may include applying a neutralizing medium on the exterior of the MnQD. The neutralizing medium may be polystyrene. The step of applying a neutralizing medium may include embedding the MnQD in the neutralizing medium. The step of embedding may be embedding the MnQD in a polystyrene bead. Tests carried out revealed that the temperature sensing of $Mn^{2+}$-doped QDs may be affected by the pH value of the solution. This can be overcome by embedding the $Mn^{2+}$-doped QDs in polystyrene beads, or by changes in the passivating and capping agents. The polystyrene beads may be >60 nm.

The method of producing an $Mn^{2+}$-doped quantum dot may include tuning the $Mn^{2+}$-doped quantum dot by adjusting the ZnS shell thickness. Tuning the $Mn^{2+}$-doped quantum dot may include increasing the ZnS protection shell thickness. Tuning the $Mn^{2+}$-doped quantum dot by increasing the ZnS protection shell thickness is illustrated in example 2.

The method of producing an $Mn^{2+}$-doped quantum dot may include tuning the $Mn^{2+}$-doped quantum dot by adjusting the $Mn^{2+}$-dopant concentration. Tuning the $Mn^{2+}$-doped quantum dot may include increasing the $Mn^{2+}$-dopant concentration. Tuning MnQDs by increasing $Mn^{2+}$ dopant concentration is illustrated in example 3. $Mn^{2+}$-dopant concentration is the average number of $Mn^{2+}$-dopant per quantum dot and has a value from 2 to 17.

Referring to FIG. 1A, a method of making water-soluble $Mn^{2+}$-doped quantum dots may include at least the first four of the following five steps:

(1) Synthesizing fluorescent semiconductor cores 110, which may be CdSSe cores. Synthesizing a CdSSe core may occur via two routes: Route A including cadmium oxide (CdO), sulfur (S), and diphenylphosphine selenide (DPPSe); or Route B including cadmium acetate (Cd(OAc)$_2$), sulfur, and selenium (Se) in 1-octadecene). Alternatively, pre-made fluorescence semiconductor cores may be provided.

(2) Growing an initial ZnS shell 120 by adding zinc stearate and sulfur alternately to form a ZnS coated core 125.

(3) Adding $Mn^{2+}$ dopants 130 by adding manganese acetate with sulfur to form an $Mn^{2+}$-doped ZnS coated core 135.

(4) Growing the ZnS protection shell by adding zinc stearate and sulfur alternately to form an $Mn^{2+}$-doped ZnS coated core with ZnS protection shell 140.

(5) Passivating the surface of the MnQDs with D-penicillamine (DPA) to produce Water-soluble MnQDs.

The method above may be adapted to replace CdSSe core synthesis and CdSSe cores with a different synthesis method and/or different fluorescent semiconductor cores. The method may also be adapted to include additional or different dopants in step 3. The method may include associating a targeting agent with the MnQD.

An embodiment provides novel MnQDs. The $Mn^{2+}$-quantum dots may include a fluorescent semiconductor core 110, an initial ZnS shell 120 covering the fluorescent semiconductor core 110, an $Mn^{2+}$ dopant 130 associated with the initial ZnS shell 120, and a ZnS protection shell 140 covering the initial ZnS shell 120 and the $Mn^{2+}$ dopant 130. The $Mn^{2+}$ dopant 130 may be associated with the initial ZnS shell by being in or on the outer surface 126 of the initial ZnS shell. Together, the $Mn^{2+}$ dopant 130, initial shell 120, and core 110 may be referred to an $Mn^{2+}$-doped ZnS coated core 135. The MnQDs may be made by any method, including but not limited to methods contained herein.

The $Mn^{2+}$ dopant of the $Mn^{2+}$-quantum dot may be referred to as an emissive dopant. In an embodiment, the $Mn^{2+}$ dopant in the $Mn^{2+}$-quantum dot may be replaced or supplemented with another emissive dopant. The emissive dopants 130 may include rare-earth ion dopants. Non-limiting examples of rare-earth ion dopants include Praseodymium ($Pr^{3+}$), Neodymium ($Nd^{3+}$), Samarium ($Sm^{3+}$), Europium ($Eu^{3+}$), Erbium ($Er^{3+}$), Dysprosium ($Dy^{3+}$), and Ytterbium ($Yb^{3+}$).

The fluorescent semiconductor core may include CdSSe. The fluorescent semiconductor core may be a cadmium-free fluorescent semiconductor core. Cadmium-free fluorescent semiconductor cores may include copper indium sulfide, zinc indium copper sulfide, and indium phosphide.

The MnQDs may include a passivating agent disposed on the ZnS protection shell. The passivation agent may be but is not limited to D-penicillamine, cystine, or dihydroplipoic acid.

The MnQDs may include a neutralizing layer. The neutralizing layer may be formed by embedding the dot in a neutralizing medium. The neutralizing medium may be but is not limited to polystyrene. The dot may be embedded in a polystyrene bead, which would be the neutralizing layer.

The MnQDs may include a targeting agent.

The MnQD may have the ZnS initial shell, or an alternate initial shell. The initial shell 120 may be a ZnS initial shell, a CdS initial shell, or a ZnSe initial shell.

The MnQD may be adapted to not include an initial shell and instead associate the emissive dopant at the interface of the fluorescent semiconductor core 110 and the protection shell 140.

The MnQD may have the ZnS protection shall, or an alternate protection shell 140. The protection shell 140 may be a ZnS protection shell, a ZnSe protection shell, or a $Zn_{1-x}Cd_xS$ protection shell, where X is the ratio Cd/(Cd+Zn) and has a value from 0 to 0.5.

Figure 8A:
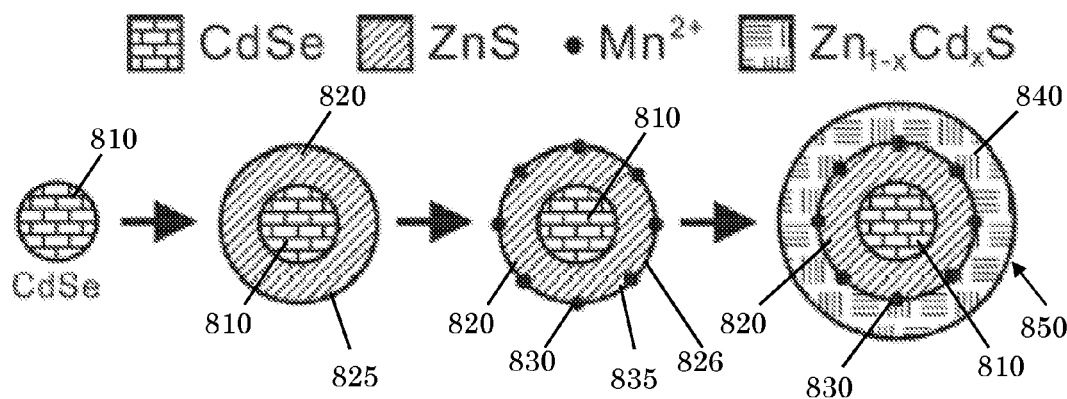
FIG. 8A illustrates the synthetic scheme for $Mn^{2+}$-doped quantum dots.
Figure 8B:
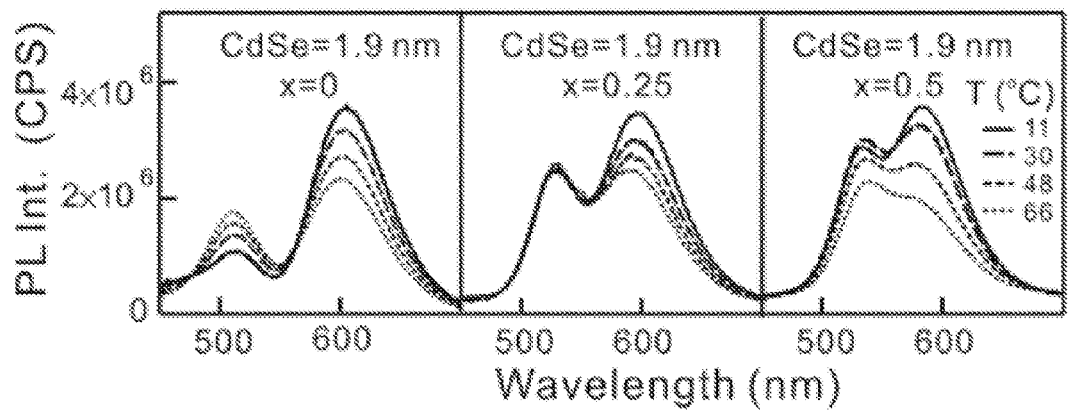
FIG. 8B illustrates temperature-dependent PL spectra of $Mn^{2+}$-doped quantum dots made with 1.9-nm CdSe cores in toluene with different Cd content (x) in the outermost shells.
Figure 8C:
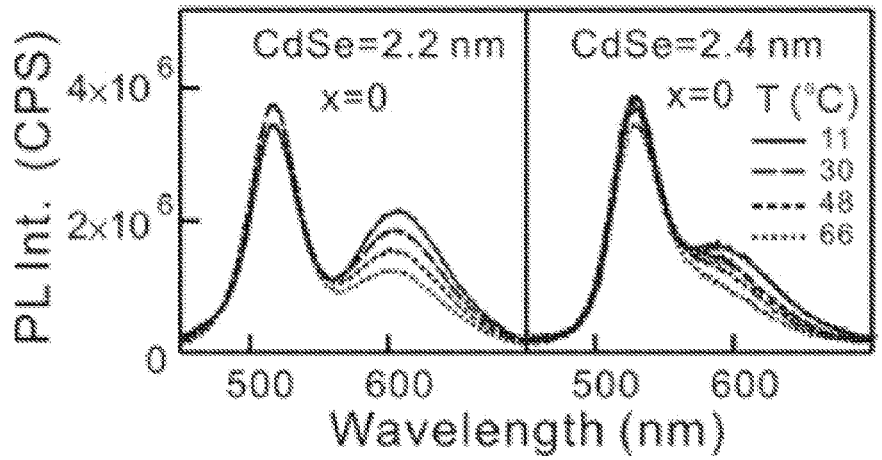
FIG. 8C illustrates temperature-dependent PL spectra of $Mn^{2+}$-doped quantum dots in toluene made with 2.2-nm and 2.4-nm CdSe cores.
Figure 8D:
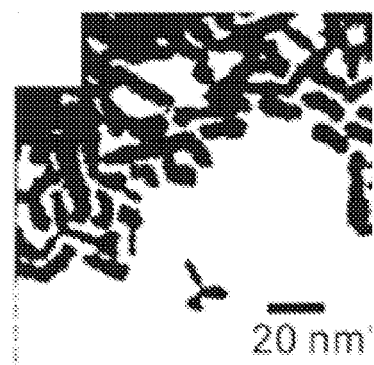
FIG. 8D illustrates a typical TEM image of the $Mn^{2+}$-doped quantum dots made with CdSe cores.

An embodiment provides a method of producing an $Mn^{2+}$ and $Cd^{2+}$ co-doped quantum dot 850, which is a variety of $Mn^{2+}$-doped quantum dot, as discussed above. Referring to FIG. 8A, the method may include preparing a CdSe core 810, coating the core with a ZnS shell 820 coating to form a ZnS coated core 825, doping the ZnS coated core 825 with an $Mn^{2+}$ dopant 830 to form an $Mn^{2+}$-doped ZnS coated core 835, and covering the $Mn^{2+}$-doped ZnS coated core 835 with a $Zn_{1-x}Cd_xS$ protection shell 840.

The $Mn^{2+}$ dopant of the $Mn^{2+}$ and $Cd^{2+}$ co-doped quantum dot may be referred to as an emissive dopant. In an embodiment, the $Mn^{2+}$ dopant in the $Mn^{2+}$ and $Cd^{2+}$ co-doped quantum dot may be replaced or supplemented with another emissive dopant. The emissive dopants 830 may include rare-earth ion dopants. Non-limiting examples of rare-earth ion dopants include Praseodymium ($Pr^{3+}$), Neodymium ($Nd^{3+}$), Samarium ($Sm^{3+}$), Europium ($Eu^{3+}$), Erbium ($Er^{3+}$), Dysprosium ($Dy^{3+}$), and Ytterbium ($Yb^{3+}$).

An embodiment includes an MnQD that is an $Mn^{2+}$ and $Cd^{2+}$ co-doped quantum dot. The $Mn^{2+}$ and $Cd^{2+}$ co-doped quantum dot may include a CdSe core 810, an initial ZnS shell covering the CdSe core 810, an $Mn^{2+}$ dopant 830 and a $Cd^{2+}$ dopant associated with the initial ZnS shell 820, and a $Zn_{1-x}Cd_xS$ protection shell 840 covering the initial ZnS shell 820 and the $Mn^{2+}$ dopant 830. X is the ratio of Cd/(Cd+Zn) in the $Zn_{1-x}Cd_xS$ protection shell 840. X may be Cd/(Cd+Zn) and has a value from 0 to 0.5. The $Mn^{2+}$ dopant 830 may be associated with the initial ZnS shell by being in or on the outer surface 826 of the initial ZnS shell. Together, the $Mn^{2+}$ dopant 830, initial shell 820, and core 810 may be referred to s an $Mn^{2+}$ and $Cd^{2+}$ co-doped ZnS coated core 835. The MnQDs may be made by any method, including but not limited to methods contained herein.

The $Mn^{2+}$ and $Cd^{2+}$ co-doped quantum dot may have the ZnS initial shell, or an alternate initial shell. The initial shell 820 may be a ZnS initial shell, a CdS initial shell, or a ZnSe initial shell.

The $Mn^{2+}$ and $Cd^{2+}$ co-doped quantum dot may be adapted to not include an initial shell and instead associate the emissive dopant at the interface of the fluorescent semiconductor core 810 and the protection shell 840.

Figure 3:
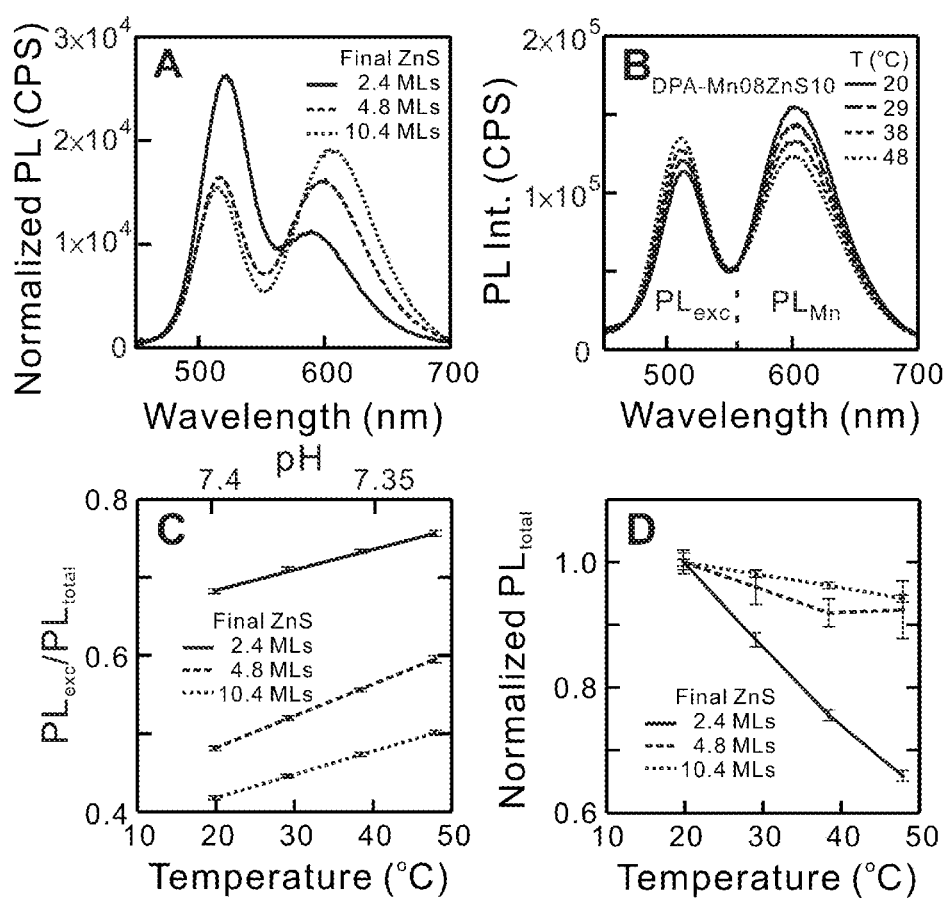
FIG. 3A illustrates the photoluminescence (PL) spectra of D-penicillamine coated $Mn^{2+}$-doped quantum dots (DPA-MnQDs) with different ZnS shell thickness measured at 20° C. The PL spectra were normalized to the integrated intensity. All of the data in FIGS. 3A-D were collected from DPA-MnQDs in 1×PBS buffer solution (pH=7.4).
FIG. 3B illustrates temperature-dependent PL spectra of DPA-Mn08ZnS10.
FIG. 3C illustrates temperature-dependent exciton emission ratio ($PL_{exc}/PL_{total}$) plots of DPA-MnQDs with different ZnS shell thickness. The pH-value axis was measured from blank 1×PBS at different temperatures.
FIG. 3D illustrates normalized temperature-dependent total intensity plots of DPA-MnQDs with different ZnS shell thickness. The plots were normalized to total PL intensity at 20° C.
Figure 5B:
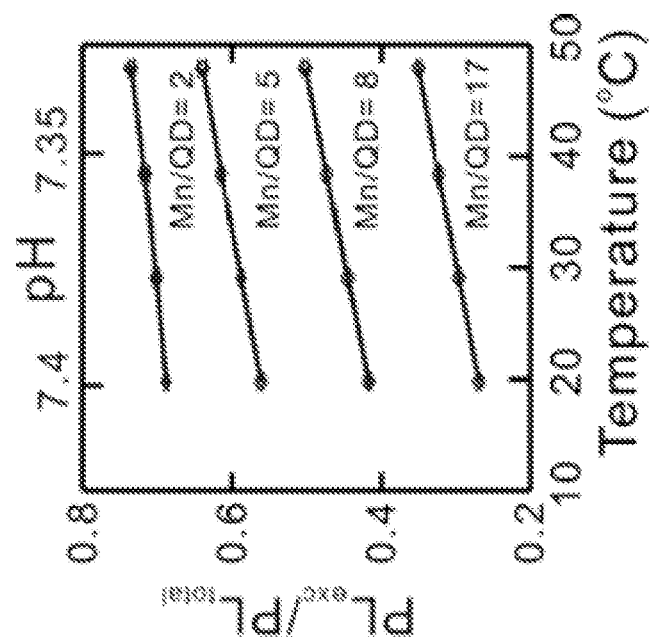
FIG. 5B illustrates temperature-dependent $PL_{exc}/PL_{total}$ plots of $Mn^{2+}$-doped quantum dots with different $Mn^{2+}$ concentration in 1×PBS buffer solution. The top pH value axis was measured from blank 1×PBS at different temperatures. The error bars are one standard deviation from the average values collected from heating-cooling cycling measurements (FIG. 6).
Figure 5A:
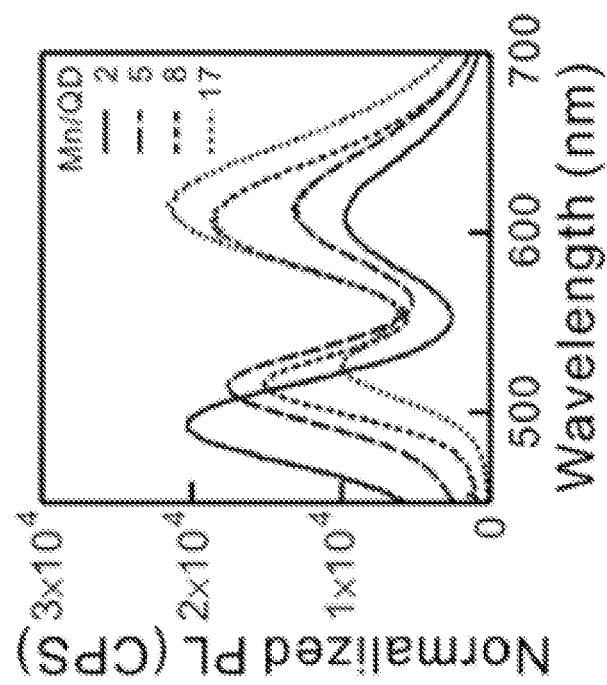
FIG. 5A illustrates PL spectra of DPA-MnQDs with different $Mn^{2+}$ concentration (Mn/QD) in 1×PBS buffer solution. The PL spectra were normalized to the integrated intensity.
Figure 9:
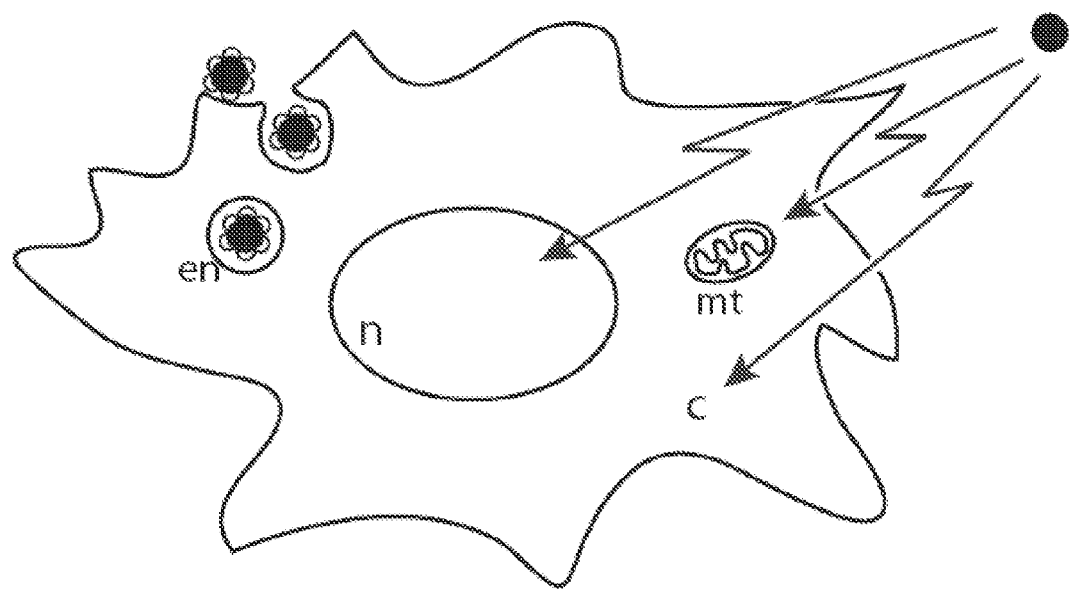
FIG. 9 illustrates delivery methods of $Mn^{2+}$-doped quantum dots to mammalian cells. Figure symbols: c=cytosol, en=endosome, mt=mitochondria, and n=nucleus.
Figures 10A, 10B, 10C:
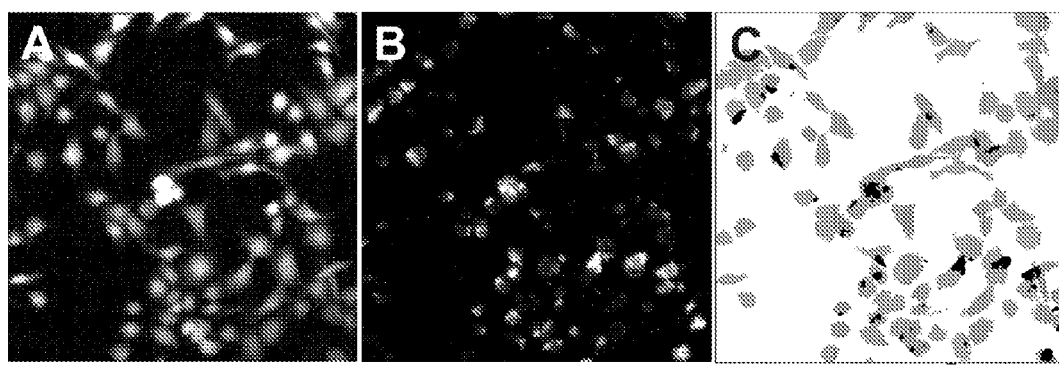
FIGS. 10A-C illustrate the viability of cells loaded with QDs after overnight recovery.

Embodiments include a method of labeling biological specimen. The method comprises contacting the biological specimen with an MnQD herein. The biological specimen may be a tissue sample, a specific cell, an intracellular organelle, an individual protein, or a cellular component. FIG. 9 illustrates delivery methods of an $Mn^{2+}$-doped quantum dot or an $Mn^{2+}$ and $Cd^{2+}$ co-doped quantum dot to mammalian cells. Delivery methods may include targeting an $Mn^{2+}$-doped quantum dot or an $Mn^{2+}$ and $Cd^{2+}$ co-doped quantum dot to the cytosol (c), endosome (en), mitochondria (mt) or nucleus (n) using a targeting agent. Targeting may be achieved by location of or mechanism of physical delivery. Targeting may be achieved by adding to the exterior of the MnQD a ligand that binds to the intended target. The ligand may but is not limited to a protein, lipid, or carbohydrate. The targeting agent may be the ligand. The method may include exciting the MnQD, measuring the excitonic emission and the $Mn^{2+}$ emission, calculating the emission intensity ratio of $PL_{exc}/PL_{total}$ and determining the temperature based on the emission intensity ratio. $PL_{exc}$ represents exciton emission intensity. $PL_{total}$ represents the integrated intensity of $PL_{exc}$ and $PL_{Mn}$. $PL_{Mn}$ represents $Mn^{2+}$ emission intensity. The isobestic point in the temperature dependent PL spectra is used to separate $PL_{exc}$ and $PL_{Mn}$ (FIG. 3B). The step of determining may include converting the difference in emission intensity ratio into difference in temperature based on the calibrated curves (FIGS. 3C and 5B). The step of determining may include performing a calibration experiment to determine the $PL_{exc}/PL_{total}$ temperature relationship, followed by measuring the ratio and using the $PL_{exc}/PL_{total}$ temperature relationship to determine the temperature. The method may include measuring the difference in temperature over space. The temperature may be determined at different time points. Exciting may include implementing an appropriate excitation device. An excitation device may include a NanoLED device, a Xeron Lamp or a laser light. Measuring the excitonic emission and $Mn^{2+}$ emission may include using a fluorometer. The fluorometer may be a Flurolog-3 fluorometer. Measuring may include using the Time-Correlated Singe Photon Counting option of the fluorometer. Measuring the exciton and $Mn^{2+}$ emission ratios may include using color filters and two photo detectors. Color filters may include two band filters for exciton and $Mn^{2+}$ emission wavelengths, or a color filter to separate exciton and $Mn^{2+}$ emission at the isosbestic point. Example calculations that may be used to in the method are illustrated in examples 1 and 11.

Embodiments include a method of sensing nanoscale temperature fluctuations in a biological material. The method may include measuring difference in temperature over time. The method may include contacting the biological material with an MnQD herein, exciting the MnQD, measuring the excitonic emission and the $Mn^{2+}$ emission, calculating the emission intensity ratio of $PL_{exc}/PL_{total}$ and determining the temperature based on the emission intensity ratio. $PL_{exc}$ represents exciton emission intensity. $PL_{total}$ represents the integrated intensity of $PL_{exc}$ and $PL_{Mn}$. $PL_{Mn}$ represents $Mn^{2+}$ emission intensity. The isobestic point in the temperature dependent PL spectra is used to separate $PL_{exc}$ and $PL_{Mn}$ (FIG. 3B). The step of determining may include converting the difference in emission intensity ratio into difference in temperature based on the calibrated curves (FIGS. 3C and 5B). The step of determining may include performing a calibration experiment to determine the $PL_{exc}/PL_{total}$ temperature relationship, followed by measuring the ratio and using the $PL_{exc}/PL_{total}$ temperature relationship to determine the temperature. The method may include measuring the difference in temperature over time. The temperature may be determined at different time points and the difference in temperature over time determined by the change in temperature at each time point. Exciting may include implementing an appropriate excitation device. An excitation device may include a NanoLED device, a Xeron Lamp or a laser light. Measuring the excitonic emission and $Mn^{2+}$ emission may include using a fluorometer. The fluorometer may be a Flurolog-3 fluorometer. Measuring may include using the Time-Correlated Singe Photon Counting option of the fluorometer. Measuring the exciton and $Mn^{2+}$ emission ratios may include using color filters and two photo detectors. Color filters may include two band filters for exciton and $Mn^{2+}$ emission wavelengths, or a color filter to separate exciton and $Mn^{2+}$ emission at the isosbestic point. Example calculations that may be used to in the method are illustrated in examples 1 and 11. The biological material may include a tissue sample, a specific cell, an intracellular organelle, an individual protein, or a cellular component. The MnQDs in this method may be targeted as described above.

Embodiments include methods of basic research of developmental biology and cancer biology using MnQDs. Embodiments include methods of diagnosis related to developmental biology and cancer biology using MnQDs.

An embodiment includes a method of sensing the local temperature of a nano- or micro-fabricated device. The method may include contacting the device with an MnQD, exciting the MnQD, measuring the excitonic emission and the $Mn^{2+}$ emissions, calculating the emission intensity ratio of $PL_{exc}/PL_{total}$ and determining the temperature from the emission intensity ratio. $PL_{exc}$ represents exciton emission intensity. $PL_{total}$ represents the integrated intensity of $PL_{exe}$ and $PL_{Mn}$. $PL_{Mn}$ represents $Mn^{2+}$ emission intensity. The isobestic point in the temperature dependent PL spectra is used to separate $PL_{exc}$ and $PL_{Mn}$ (FIG. 3B). The step of determining may include converting the difference in emission intensity ratio into difference in temperature based on the calibrated curves (FIGS. 3C and 5B). The step of determining may include performing a calibration experiment to determine the $PL_{exc}/PL_{total}$ temperature relationship, followed by measuring the ratio and using the $PL_{exc}/PL_{total}$ temperature relationship to determine the temperature. The method may include measuring the difference in temperature over time or space. The temperature may be determined at different points in space and/or time, and the difference in temperature over space and/or time determined by the change in temperature at each point. Exciting may include implementing an appropriate excitation device. An excitation device may include a NanoLED device, a Xeron Lamp or a laser light. Measuring the excitonic emission and $Mn^{2+}$ emission may include using a fluorometer. The fluorometer may be a Flurolog-3 fluorometer. Measuring may include using the Time-Correlated Singe Photon Counting option of the fluorometer. Measuring the exciton and $Mn^{2+}$ emission ratios may include using color filters and two photo detectors. Color filters may include two band filters for exciton and $Mn^{2+}$ emission wavelengths, or a color filter to separate exciton and $Mn^{2+}$ emission at the isosbestic point. Example calculations that may be used to in the method are illustrated in examples 1 and 11. The MnQD may be targeted as described above, where the ligands are specific to structures in the nano- or micro-fabricated device.

Embodiments include a method of sensing temperature. The method comprises contacting a sample with an MnQD herein. The sample may be a biological or non-biological sample. Examples of the biological sample include but are not limited to a tissue sample, a specific cell, an intracellular organelle, an individual protein, or a cellular component. Examples of a non-biological sample include but are not limited nano- or micro-fabricated devices. Targeting may be achieved as discussed above. The method may include exciting the MnQD, measuring the excitonic emission and the $Mn^{2+}$ emission, calculating the emission intensity ratio of $PL_{exc}/PL_{total}$ and determining the temperature based on the emission intensity ratio. $PL_{exc}$ represents exciton emission intensity. $PL_{total}$ represents the integrated intensity of $PL_{exc}$ and $PL_{Mn}$. $PL_{Mn}$ represents $Mn^{2+}$ emission intensity. The isobestic point in the temperature dependent PL spectra is used to separate $PL_{exc}$ and $PL_{Mn}$ (FIG. 3B). The step of determining may include converting the difference in emission intensity ratio into difference in temperature based on the calibrated curves (FIGS. 3C and 5B). The step of determining may include performing a calibration experiment to determine the $PL_{exc}/PL_{total}$ temperature relationship, followed by measuring the ratio and using the $PL_{exc}/PL_{total}$ temperature relationship to determine the temperature. The method may include measuring the difference in temperature over time and/or space. The temperature may be determined at different points in space and/or time, and the difference in temperature over space and/or time determined by the change in temperature at each point. Exciting may include implementing an appropriate excitation device. An excitation device may include a NanoLED device, a Xeron Lamp or a laser light. Measuring the excitonic emission and $Mn^{2+}$ emission may include using a fluorometer. The fluorometer may be a Flurolog-3 fluorometer. Measuring may include using the Time-Correlated Singe Photon Counting option of the fluorometer. Measuring the exciton and $Mn^{2+}$ emission ratios may include using color filters and two photo detectors. Color filters may include two band filters for exciton and $Mn^{2+}$ emission wavelengths, or a color filter to separate exciton and $Mn^{2+}$ emission at the isosbestic point. Example calculations that may be used to in the method are illustrated in examples 1 and 11.

The MnQDs herein are a new class of quantum dots and show excellent temperature sensitivity and ratiometric temperature sensing in both organic solvents and water-based solutions. Methods of synthesis of MnQDs herein may utilize air-stable and inexpensive chemicals that can significantly reduce the cost of manufacture and chemical storage, as well as minimizing the risk associated with handling flammable chemicals. Moreover, the use of a stepwise synthesis scheme in the methods of synthesis herein offers opportunities to tune the optical properties and temperature-sensing behaviors by varying the structural parameters at each step, allowing the preparation of customized $Mn^{2+}$-doped quantum dots.

The MnQDs herein have potential applications in biological labeling and sensing. They may be used for probing the local temperature inside a single living cell, of living cells in a tissue sample, and so forth. For example, the MnQDs may be used in methods designed to understand the thermogenesis (generation of heat) of living cells and correlate the observation to the metabolic state of the cell. The insights could be relevant to disease diagnosis and prevention. For example, one may use the MnQD based temperature sensor to test the hypothesis that cancerous cells generate more heat than health cells due to their high metabolic activity. Or, one may study how temperature and temperature gradients impact on stem cell differentiation.

MnQDs herein may be utilized in any setting where nanoscale temperature sensing is desired. A non-limiting example is to use the MnQDs during an integrated circuit chip development process. The insulator layer in the integrated circuits is very important. The newest development is to replace the inorganic materials with organic materials for the insulating layer to cut down the price and weight. However, organic insulators are much more sensitive to temperature-related degradation pathways. That imposes an additional constraint on the circuit design to keep the heat production low and homogeneous across an integrated circuit chip. Therefore, the circuit design/process development will benefit from knowing exactly where the heat is being generated.

EMBODIMENTS

The following list includes particular embodiments of the present invention. The list, however, is not limiting and does not exclude alternate embodiments, as would be appreciated by one of ordinary skill in the art.

1. An $Mn^{2+}$-doped quantum dot comprising:
a fluorescent semiconductor core;
an initial shell covering the fluorescent semiconductor core, wherein the initial shell is an initial ZnS shell, an initial CdS shell, or an initial ZnSe shell;
an $Mn^{2+}$ dopant associated with the initial shell; and
a protection shell covering the initial shell and the $Mn^{2+}$ dopant, wherein the protection shell is a ZnS protection shell, a ZnSe protection shell, or a $Zn_{1-x}Cd_xS$ protection shell, wherein X is the ratio of Cd/(Cd+Zn) in the $Zn_{1-x}Cd_xS$ protection shell and has a value from 0 to 0.5.

2. The composition of embodiment 1, wherein the fluorescent semiconductor core includes CdSSe.

3. The composition of any one or more of embodiments 1 and 2, wherein the fluorescent semiconductor core includes a substance selected from the group consisting of copper indium sulfide, zinc indium copper sulfide, and indium phosphide.

4. The composition of any one or more of embodiments 1-3, wherein the $Mn^{2+}$-doped quantum dot includes a neutralizing layer.

5. The composition of embodiment 4, wherein the neutralizing layer includes polystyrene.

6. The composition of embodiment 5, wherein the neutralizing layer is a polystyrene bead and the $Mn^{2+}$-doped quantum dot is embedded in the polystyrene bead.

7. The composition of any one or more of embodiments 1-6 further comprising a passivating agent associated with the protection shell.

8. The composition of embodiment 7, wherein the passivating agent is D-penicillamine.

9. The composition of embodiment 7, wherein the passivating agent is cystine.

10. The composition of embodiment 7, wherein the passivating agent is selected from the group consisting of dihydrolipoic acid, dihydrolipoic acid derivatives, a polyethylene glycol functionalized dihydrolipoic acid, and an —SH group functionalized passivating agent.

11. An $Mn^{2+}$ and $Cd^{2+}$ co-doped quantum dot comprising:
a CdSe core;
an initial shell covering the CdSe core, wherein the initial shell is an initial ZnS shell, an initial CdS shell, or an initial ZnSe shell;
an $Mn^{2+}$ dopant associated with the initial shell; and
a $Zn_{1-x}Cd_xS$ protection shell covering the initial shell and the $Mn^{2+}$ dopant, wherein X is the ratio of Cd/(Cd+Zn) in the $Zn_{1-x}Cd_xS$ protection shell and has a value from 0 to 0.5.

12. A method of producing an $Mn^{2+}$-doped quantum dot comprising:
providing a fluorescent semiconductor core;
coating the fluorescent semiconductor core with an initial shell to form a coated core, wherein the initial shell is an initial ZnS shell, an initial CdS shell, or an initial ZnSe shell;
doping the coated core with $Mn^{2+}$ to form an $Mn^{2+}$-doped coated core; and
covering the $Mn^{2+}$-doped coated core with a protection shell wherein the protection shell is a ZnS protection shell, a ZnSe protection shell, or a $Zn_{1-x}Cd_xS$ protection shell, wherein X is the ratio of Cd/(Cd+Zn) in the $Zn_{1-x}Cd_xS$ protection shell and has a value from 0 to 0.5.

13. The method of embodiment 12, wherein the fluorescent semiconductor core includes CdSSe.

14. The method of embodiment 12, wherein providing the fluorescent semiconductor core includes forming the core from cadmium oxide, sulfur and diphenyl phosphine selenide.

15. The method of any one or more of embodiments 13-14, wherein forming includes injecting a sulfur selenium precursor solution comprising sulfur, diphenylphosphine selenide and 1-octadiene into a cadmium precursor solution comprising cadmium oxide, oleic acid and 1-octadiene.

16. The method of any one or more of embodiments 13-14, wherein providing the fluorescent semiconductor core includes forming the core from cadmium acetate, sulfur and selenium in 1-octadecene.

17. The method of embodiment 16, wherein forming includes:
heating cadmium acetate dihydrate, 1-octadiene and oleic acid;
cooling the resulting solution;
and adding selenium and sulfur in the cooled solution containing cadmium precursor.

18. The method of embodiment 17, wherein the step of adding includes adding selenium powder and sulfur powder into the cooled resulting solution containing cadmium, and heating the mixture containing cadmium, sulfur, and selenium.

19. The method of embodiment 12, wherein the fluorescent semiconductor core includes a substance selected from the group consisting of copper indium sulfide, zinc indium copper sulfide, and indium phosphide.

20. The method of any one or more of embodiments 12-19 further comprising embedding the $Mn^{2+}$-doped quantum dot in a neutralizing medium.

21. The method of embodiment 20, wherein the neutralizing medium is polystyrene.

22. The method of any one or more of embodiments 12-21 further comprising passivating the $Mn^{2+}$-doped quantum dot with a passivating agent.

23. The method of embodiment 22, wherein the passivating agent is D-penicillamine.

24. The method of embodiment 22, wherein the passivating agent is cystine.

25. The method of embodiment 22, wherein the passivating agent is selected from the group consisting of dihydrolipoic acid, dihydrolipoic acid derivatives, a polyethylene glycol functionalized dihydrolipoic acid, and an —SH group functionalized passivating agent.

26. The method of any one or more of embodiments 12-25 further comprising tuning the $Mn^{2+}$-doped quantum dot by adjusting at least one of the initial shell or the protection shell thickness.

27. The method of any one or more of embodiments 12-26 further comprising tuning the $Mn^{2+}$-doped quantum dot by adjusting the $Mn^{2+}$-dopant concentration.

28. A method of producing an $Mn^{2+}$ and $Cd^{2+}$ co-doped quantum dot comprising:
providing a CdSe core;
coating the CdSe core with an initial shell coating to form a coated core, wherein the initial shell is an initial ZnS shell, an initial CdS shell, or an initial ZnSe shell;
doping the coated core with $Mn^{2+}$ to form an $Mn^{2+}$-doped coated core; and
covering the $Mn^{2+}$-doped coated core with a $Zn_{1-x}Cd_xS$ protection shell, wherein X is the ratio of Cd/(Cd+Zn) in the $Zn_{1-x}Cd_xS$ protection shell and has a value from 0 to 0.5.

29. The method of embodiment 28 further comprising embedding the $Mn^{2+}$ and $Cd^{2+}$ co-doped quantum dot in a neutralizing medium.

30. The method of embodiment 30, wherein the neutralizing medium is polystyrene.

31. The method of any one or more of embodiments 28-30 further comprising passivating the $Mn^{2+}$ and $Cd^{2+}$ co-doped quantum dot with a passivating agent.

32. The method of embodiment 31, wherein the passivating agent is D-penicillamine.

33. The method of embodiment 31, wherein the passivating agent is cystine.

34. The method of embodiment 31, wherein the passivating agent is selected from the group consisting of dihydrolipoic acid, dihydrolipoic acid derivatives, a polyethylene glycol functionalized dihydrolipoic acid, and an —SH group functionalized passivating agent.

35. The method of any one or more of embodiments 28-34 further comprising tuning the $Mn^{2+}$ and $Cd^{2+}$ co-doped quantum dot by adjusting at least one of the initial ZnS shell coating or $Zn_{1-x}Cd_xS$ protection shell thickness.

36. The method of any one or more of embodiments 28-35 further comprising tuning the $Mn^{2+}$ and $Cd^{2+}$ co-doped quantum dot by adjusting the $Mn^{2+}$-dopant concentration.

37. A method of labeling a biological specimen comprising: contacting the biological specimen with an $Mn^{2+}$-doped quantum dot.

38. The method of embodiment 37, wherein the $Mn^{2+}$-doped quantum dot is the $Mn^{2+}$-doped quantum dot of any one or more of embodiments 1-10, the $Mn^{2+}$ and $Cd^{2+}$ co-doped quantum dot of embodiment 11, or an $Mn^{2+}$-doped quantum dot made by the method of any one or more of embodiments 12-36.

39. The method of any one or more of embodiments 37 or 38 further comprising:
exciting the $Mn^{2+}$-doped quantum dot;
measuring the excitonic emission and $Mn^{2+}$ emission;
calculating the emission intensity ratio; and
determining the temperature of the biological specimen based on the emission intensity ratio.

40. The method of any one or more of embodiments 37-39, wherein the $Mn^{2+}$-doped quantum dot is an $Mn^{2+}$ and $Cd^{2+}$ co-doped quantum dot.

41. The method of any one or more of embodiments 37-40, wherein the biological specimen is a tissue, a cell, an intracellular organelle, an individual protein or a cellular component.

42. A method of sensing nanoscale temperature fluctuations in a biological material comprising:
contacting the biological material with an $Mn^{2+}$-doped quantum dot;
exciting the $Mn^{2+}$-doped quantum;
measuring the excitonic emission and $Mn^{2+}$ emission;
calculating the emission intensity ratio; and
determining the temperature based on the emission intensity ratio.

43. The method of embodiment 42, wherein the $Mn^{2+}$-doped quantum dot is the $Mn^{2+}$-doped quantum dot of any one or more of embodiments 1-10, the $Mn^{2+}$ and $Cd^{2+}$ co-doped quantum dot of embodiment 11, or an $Mn^{2+}$-doped quantum dot made by the method of any one or more of embodiments 12-36.

44. The method of any one or more of embodiments 42-43, wherein the biological material is a cell, a tissue, an intracellular organelle, an individual protein or a cellular component.

45. The method of any one or more of embodiments 42-44, wherein the $Mn^{2+}$-doped quantum dot is an $Mn^{2+}$ and $Cd^{2+}$ co-doped quantum dot.

46. The method of any one or more of embodiments 42-45, wherein the $Mn^{2+}$-doped quantum dot includes a targeting agent.

47. The method of embodiment 46, wherein the targeting agent is a ligand that binds a target selected from the group consisting of cytosol, endosome, mitochondria or nucleus.

48. A method of sensing the local temperature of a nano- or micro-fabricated device comprising:
contacting the nano- or micro-fabricated device with an $Mn^{2+}$-doped quantum dot;
exciting the $Mn^{2+}$-doped quantum dot;
measuring the excitonic emission and $Mn^{2+}$ emission;
calculating the emission intensity ratio; and
determining the temperature based on the emission intensity ratio.

49. The method of embodiment 48, wherein the $Mn^{2+}$-doped quantum dot is the $Mn^{2+}$-doped quantum dot of any one or more of embodiments 1-10, the $Mn^{2+}$ and $Cd^{2+}$ co-doped quantum dot of embodiment 11, or an $Mn^{2+}$-doped quantum dot made by the method of any one or more of embodiments 12-36.

50. The method of any one or more of embodiments 46-49, wherein the $Mn^{2+}$-doped quantum dot is an $Mn^{2+}$ and $Cd^{2+}$ co-doped quantum dot.

51. A method of sensing temperature in a sample comprising:
contacting the sample with an $Mn^{2+}$-doped quantum dot.

52. The method of embodiment 51, wherein the $Mn^{2+}$-doped quantum dot is the $Mn^{2+}$-doped quantum dot of any one or more of embodiments 1-10, the $Mn^{2+}$ and $Cd^{2+}$ co-doped quantum dot of embodiment 11, or an $Mn^{2+}$-doped quantum dot made by the method of any one or more of embodiments 12-36.

53. The method of any one or more of embodiments 51-52 further comprising:
exciting the $Mn^{2+}$-doped quantum dot;
measuring the excitonic emission and $Mn^{2+}$ emission;
calculating the emission intensity ratio; and
determining the temperature of the sample based on the emission intensity ratio.

54. The method of any one or more of embodiments 51-53, wherein the $Mn^{2+}$-doped quantum dot is an $Mn^{2+}$ and $Cd^{2+}$ co-doped quantum dot.

Further embodiments herein may be formed by supplementing an embodiment with one or more element from any one or more other embodiment herein, and/or substituting one or more element from one embodiment with one or more element from one or more other embodiment herein.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

Example 1—Synthetic Scheme for Temperature-Sensitive DPA-Coated $Mn^{2+}$-Doped Quantum Dots $Mn^{2+}$-doped quantum dots and the rare earth-doped materials share a similar principle by which the temperature can be read out through the ratio of two energetically proximate emission bands (Wade et al., 2003, J. Appl. Phys., 94, 4743-56; Vlaskin et al., 2010, Nano Lett., 10, 3670-74, which are incorporated herein by reference as if fully set forth). Such an emission intensity ratio (EIR) scheme for temperature sensing has been extensively studied in rare earth-doped materials (see Wade et al., 2003, J. Appl. Phys., 94, 4743-56 for review). Briefly, the EIR scheme utilizes the relative emission intensities from two closely separated energy levels of a single rare earth ion dopant. When the two energy levels are thermally coupled to reach thermal equilibrium, the population of the two levels can be described by a Boltzmann-type distribution parameterized by temperature. The relative populations of the two energy levels (a function of temperature) can be approximated using the intensity ratio of the emission from the two thermally coupled levels, providing information of the surrounding temperature. To obtain reliable information from the emission intensity ratio (e.g., sufficient number of photons detected), the mechanism put forth by the study of rare earth-doped materials highlights the necessity to have radiative transitions dominate over nonradiative transitions (Wade et al., 2003, J. Appl. Phys., 94, 4743-56, which is incorporated herein by reference as if fully set forth). In addition, the energy separation between the two states should be small in order for efficient thermal coupling, but it should not be too small such that the two emission bands become indistinguishable. For MnQDs, it should be possible to change the temperature-sensing capacity without replacing dopants and host materials because the separation between the two emissive states can be easily tuned by varying the band gap of the semiconductor nanocrystals (Murray et al., 1993, J. Am. Chem. Soc., 115, 8706-15; Bailey and Nie, 2003, J. Am. Chem. Soc., 125, 7100-06; Zhong et al., 2003, J. Am. Chem. Soc., 125, 8589-94, which are incorporated herein by reference as if fully set forth).

Figure 1D:
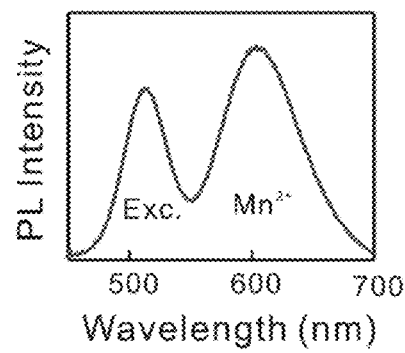
FIG. 1D illustrates a typical photoluminescence (PL) spectrum of water-soluble DPA-MnQDs. Two emissions are shown; an exciton emission and an $Mn^{2+}$ emission.
Figure 1E:
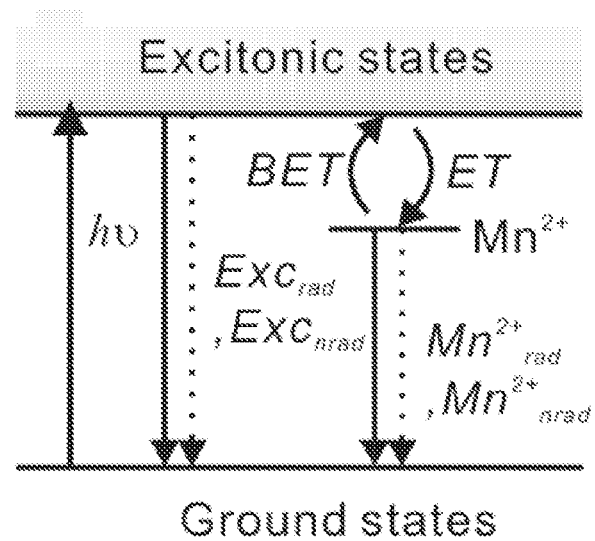
FIG. 1E illustrates a schematic energy diagram of $Mn^{2+}$-doped quantum dots adapted from Vlaskin et al., 2010, Nano Lett, 10, 3670-74, which is incorporated herein by reference as if fully set forth. ET and BET represent energy transfer and back energy transfer, respectively. $Exc_{rad}$, $Exc_{nrad}$ represent radiative and nonradiative exciton relaxations, respectively. $Mn^{2+}_{rad}$, and $Mn^{2+}_{nrad}$ respectively represent radiative and nonradiative relaxations from $Mn^{2+}$ excited states.
Figure 2:
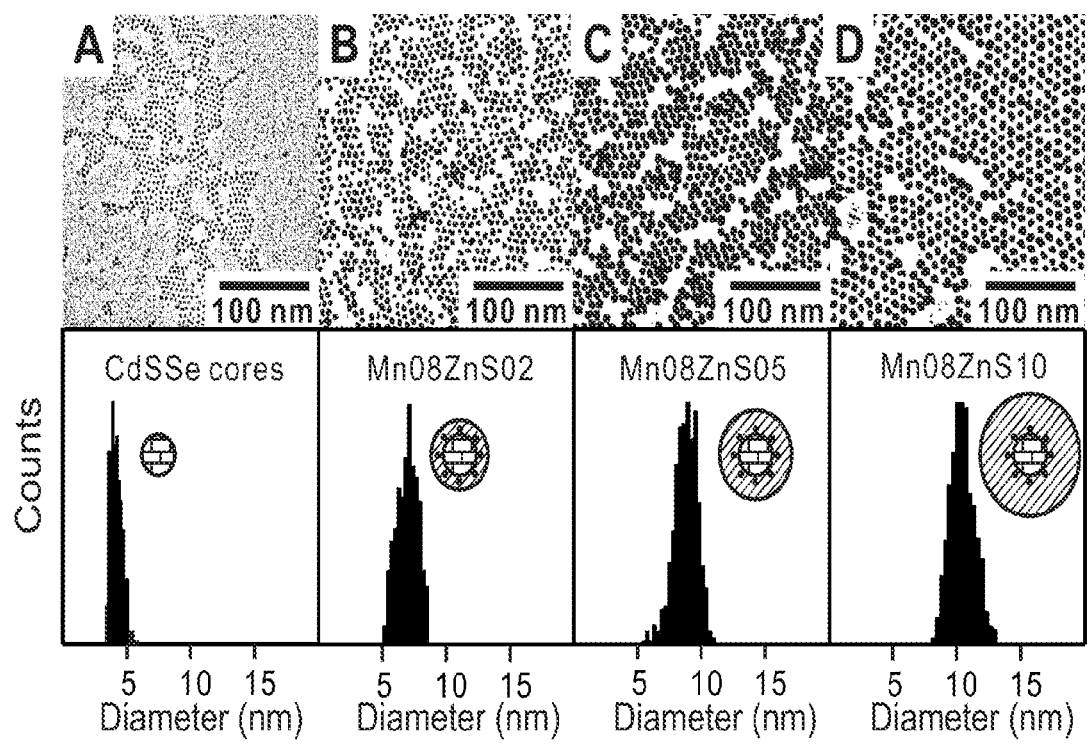
FIG. 2A illustrates a representative TEM image of CdSSe cores.
FIGS. 2B-D illustrate representative TEM images of MnQDs with 2.4, 4.8, and 10.4 monolayers of ZnS protection shells (ZnS02, ZnS05, and ZnS10) after growth of 1.6 MLs of ZnS shells and doping of Mn cations, respectively. The average $Mn^{2+}$ dopant per quantum dot (Mn/QD) was 8 (Mn08), measured by inductively coupled plasma mass spectroscopy (ICP-MS). The bottom panel shows size distribution histograms. The average diameters of CdSSe, Mn08ZnS02, Mn08ZnS05, and Mn08ZnS10 are 4.2, 7.0, 8.7, and 10.4 nm, respectively.

The temperature-sensing mechanism of $Mn^{2+}$-doped quantum dots can be understood by a dual emission model (FIG. 1E) as put forth by Vlaskin et al., analogous to the aforementioned picture for the rare earth-doped materials (Vlaskin et al., 2010, Nano Lett., 10, 3670-74, which is incorporated herein by reference as if fully set forth). The energy separation between two emission peaks (from the excitonic states and the $Mn^{2+}$ dopant states) in $Mn^{2+}$-doped quantum dots (FIG. 1D), however, is greater than that of a typical rare-earth ion. An outline of the $Mn^{2+}$-doped quantum dots sensing mechanism is provided here. The energy separation in $Mn^{2+}$-doped quantum dots allows a small fraction of energy in the $Mn^{2+}$ excited states to thermally repopulate the quantum dot's excitonic states based on the Boltzmann-type distribution. If a comparable energy separation existed in rare-earth ions, temperature sensitivity would not have been observed. $Mn^{2+}$-doped quantum dots, conversely, show excellent ratiometric temperature sensing behavior (Vlaskin et al., 2010, Nano Lett., 10, 3670-74, which is incorporated herein by reference as if fully set forth). This result occurs because the relative lifetimes in the $Mn^{2+}$-doped quantum dots between the excitonic states (10's of ns) and the $Mn^{2+}$-dopant states (~2 ms) are drastically different. Even though the thermally repopulated excitonic population is quite small, the significantly faster radiative decay rate of the excitonic state relative to that of the $Mn^{2+}$-dopant state allows for additional exciton emission signal to be observed over the lifetime of $Mn^{2+}$ emission. This rationale implies a rapid thermal equilibrium between the excitonic and the $Mn^{2+}$-dopant states. Therefore, the timescale of the energy equilibration process—which includes the energy transfer (ET, from the excitonic state to the $Mn^{2+}$ excited state) and the back energy transfer (BET, from the $Mn^{2+}$ excited state to the excitonic state) must be much shorter than the lifetimes of both the exciton and the $Mn^{2+}$ emissions. Fast ET between a single pair of exciton and $Mn^{2+}$ dopant (~60 ps, most likely dependent on the configuration details of the system) has been reported by Chen et al. in $Mn^{2+}$-doped (CdS)ZnS (core)shell nanocrystals (Chen et al., 2010, J. Phys. Chem. C, 114, 4418-23, which is incorporated herein by reference as if fully set forth). In addition, Vlaskin et al. have reported the timescale of ET to be shorter than 20 ps in the $(Zn_{1-x}Mn_xSe)ZnCdSe$ (core)shell nanocrystals and suggested that the timescale for BET should also be short, although the timescale for BET was not directly measured (Vlaskin et al., 2010, Nano Lett., 10, 3670-74, which is incorporated herein by reference as if fully set forth).

The (core)shell structure was chosen as the base configuration because it allows independent tuning of the composition and size of the core, the composition and thickness of the shell, and the $Mn^{2+}$ dopant amount. The core serves as the primary excitonic emission source whereas the shell hosts the $Mn^{2+}$ dopant. ZnS was chosen as the host shell material to take advantage of the extensive knowledge on water-soluble ligands designed for this surface. Here, D-penicillamine (DPA), which is inexpensive and commercially available, is used to demonstrate water solubility; nevertheless, it should be noted that other types of passivating agents are expected to work as well. DPA-coated QDs have been shown to be stable over a wide pH range and exhibit weak nonspecific binding to cells (Breus et al., 2009, ACS Nano, 3, 2573-80, which is incorporated herein by reference as if fully set forth). This stability has been attributed to the zwitterionic terminal of DPA and the thiol functional group surrounded by two methyl groups, which create steric constraints against oxidative dimerization of thiol ligands (Breus et al., 2009, ACS Nano, 3, 2573-80, which is incorporated herein by reference as if fully set forth).

With the shell material chosen, a new accessible synthetic procedure was designed that retains the excellent temperature sensitivity of MnQDs. One of the most common core compositions for ZnS-shelled QDs is CdS. The synthetic procedure for $Mn^{2+}$-doped (CdS)ZnS nanocrystals reported by Yang et al. met the greener-approach criteria—it uses air-stable and inexpensive chemicals (Yang et al., 2006, J. Am. Chem. Soc., 128, 12428-29; Yang et al., 2008, 130, 15649-61, which are incorporated herein by reference as if fully set forth). That procedure also affords the flexibility to tune the optical properties by modifying the structure of the MnQDs, e.g., the radial position of $Mn^{2+}$-dopant and the $Mn^{2+}$ concentration. Ratiometric temperature sensing, however, was not observed in their $Mn^{2+}$-doped (CdS)ZnS nanocrystals. This is because the excitonic state of the (CdS)ZnS quantum dot has a much higher energy than the excited-state of $Mn^{2+}$ dopant such that an efficient thermal coupling between the two cannot be achieved. By doping the CdS core (bulk CdS band gap ~2.42 eV) with CdSe (bulk CdSe band gap ~1.74 eV), yielding $CdS_{1-x}Se_x$ core composition, the excitonic emission was brought closer to the $Mn^{2+}$ excited state to allow efficient coupling. The simplified designation, CdSSe, is used to indicate the core composition.

A synthetic scheme for temperature-sensitive DPA-coated $Mn^{2+}$-doped quantum dots is illustrated in FIG. 1A., for which the detailed synthetic procedure and parameters are contained in examples 1 and 4-9. This synthetic procedure does not require the use of the glovebox and can be carried out by simply using Schlenk lines and inexpensive, air-stable chemicals via Route B. To further simplify the synthetic procedure, three steps (step 2-4 in FIG. 1A) are combined and performed in the same flask. Based on the previously published reports, the $Mn^{2+}$ ions are likely sandwiched between the initial thin ZnS-shell coating and the thicker protective ZnS shell (Yang et al., 2006, J. Am. Chem. Soc., 128, 12428-29; Yang et al., 2008, 130, 15649-61, which are incorporated herein by reference as if fully set forth). The thicker external shell is one of the factors that allows retention of temperature sensitivity of this base structure in water. Synthesizing customized MnQDs for specific measurement applications is possible because this procedure permits great flexibility in tuning MnQD optical properties by varying their structure and composition. For example, the optical properties of MnQDs can be tuned by varying the size of cores and composition of shells (FIG. 8). Here, two parameters that impact temperature sensitivity in water-soluble MnQDs using CdSSe cores—the external ZnS shell thickness and the $Mn^{2+}$ dopant content are shown.

Example 2—Tuning $Mn^{2+}$-Doped Quantum Dots by Increasing External ZnS Shell Thickness For robust ratiometric temperature sensing, radiative transitions should dominate the nonradiative transitions so that a sufficient number of photons can be detected. The ZnS shell thickness may play a role for ratiometric temperature sensing in MnQDs. To examine this parameter systematically, a series of MnQDs with different shell thicknesses were synthesized. To avoid batch-to-batch variations, the samples were prepared from the same intermediate MnQDs (the intermediate MnQD structure after step 3 in FIG. 1A). TEM images of the CdSSe cores and the final MnQDs show that the size of the spherical nanocrystals increases with the nominal shell thickness (FIGS. 2A-2D). This series of samples are called DPA-Mn08ZnS02, DPA-Mn08ZnS05, and DPA-Mn08ZnS10 for DPA-MnQDs (Mn/QD=8) with 2.4, 4.8, and 10.4 monolayers (MLs) of external ZnS shell after the growth of nominally 1.6 MLs of ZnS shells and doping of Mn cations, respectively. The PL quantum yields of the DPA-MnQD samples reported here are tabulated in Table 1, below.

TABLE 1

Temperature sensitivity, precision of temperature sensing, quantum yields, and estimated percentages of undoped quantum dots of DPA-MnQDs

| Sample name | Temperature sensitivity* | Precision** | Quantum yield | Undoped dots*** (%) |
| --- | --- | --- | --- | --- |
| DPA-Mn08ZnS02 | $(2.6 \pm 0.3) \times 10^{-3}$ °C.$^{-1}$ | $2.29 \pm 0.42$° C. | 14% | $7.55 \pm 0.03$ |
| DPA-Mn08ZnS05 | $(4.0 \pm 0.4) \times 10^{-3}$ °C.$^{-1}$ | $1.61 \pm 0.43$° C. | 11% | $3.05 \pm 0.06$ |
| DPA-Mn08ZnS10 | $(3.0 \pm 0.3) \times 10^{-3}$ °C.$^{-1}$ | $1.68 \pm 0.27$° C. | 13% | $6.8 \pm 0.06$ |
| DPA-Mn02ZnS10 | $(1.7 \pm 0.3) \times 10^{-3}$ °C.$^{-1}$ | $2.19 \pm 0.66$° C. | 17% | $14.7 \pm 0.2$ |
| DPA-Mn05ZnS10 | $(3.1 \pm 0.1) \times 10^{-3}$ °C.$^{-1}$ | $0.59 \pm 0.20$° C. | 14% | $14.1 \pm 0.1$ |
| DPA-Mn17ZnS10 | $(3.0 \pm 0.1) \times 10^{-3}$ °C.$^{-1}$ | $0.79 \pm 0.07$° C. | 8% | $3.37 \pm 0.07$ |

*Temperature sensitivity was obtained from the slopes of temperature-dependent $PL_{exc}/PL_{total}$ plots of DPA-MnQDs. The error bars are one standard deviation from the average values collected from heating-cooling cycling measurements.
**The precision of temperature sensing (temperature-dependent uncertainty of measurement), for each sample, was the average value for uncertainties obtained at different temperatures over the heating-cooling cycles.
***The percentages of undoped quantum dots were estimated based on the lifetime traces (see example 11).

The photoluminescence (PL) spectra of this MnQD series are shown in FIG. 3A. One can see that as the ZnS shell thickness increases, the exciton emission band (~520 nm) shifts to the blue whereas the $Mn^{2+}$ emission band (~600 nm) shifts to the red. The red shift of $Mn^{2+}$ emission band is attributed to the increase in lattice pressure with increasing ZnS shell thickness (Ithurria et al., 2007, Phys. Rev. Lett., 99, 265501; Chen et al., 2001, J. Appl. Phys., 89, 1120-29, which are incorporated herein by reference as if fully set forth). The blue shift of exciton emission could be due to minor alloying of the nanocrystals because the final ZnS coating was performed at 280° C.—a temperature at which alloying can occur. In addition, the relative intensity of the exciton emission decreases with increasing ZnS shell thickness. This is attributed to a reduced contribution of BET with thicker ZnS shells, resulting from the increase of energy separation between the excitonic and the $Mn^{2+}$ states. Based on a previous study, alloying of (ZnSe)CdSe (core) shell nanocrystals begin at 270-280° C., and the alloying process accelerates at temperatures higher than 290° C. (Zhong et al., 2003, J. Am. Chem. Soc., 125, 8589-94, which is incorporated herein by reference as if fully set forth). Therefore, the temperature for ZnS shell coating should not be higher than 280° C. to avoid the formation of homogenously alloyed nanocrystals, resulting in significant decrease of exciton emission. To avoid alloying of the MnQDs, the ZnS shell growth was performed at a lower temperature (220° C.), and the exciton emission peaks of the MnQDs were not blue-shifted, indicating no observable alloying. Unfortunately, the MnQDs using lower temperature in the ZnS shell coating did not exhibit reversible temperature sensing behavior in water-based solution. Therefore, high temperature is necessary for the ZnS shell coating procedure to maintain the reversible temperature sensing.

The temperature dependence of DPA-MnQD spectroscopic response with different shell thicknesses is generally similar. As a representative example, FIG. 3B shows the PL typical lifetime for exciton emission in quantum dots and therefore assigned to the exciton emission. The constant plateau intensity in the lifetime trace is seen to increase with temperature. It appears flat in the 200-ns lifetime acquisition window because $Mn^{2+}$ dopants have long-lived excited states (lifetime 2 ms) and only a small fraction of energy is transferred back to the excitonic states from the $Mn^{2+}$ excited states via BET. The temperature-dependent plateau intensity is attributed to contributions from BET, originated from temperature-dependent Boltzmann-type distribution (see Table 2, below, for temperature-dependent plateau intensity). Indeed, the measured lifetimes of the PL decays beyond 200 ns were on the order of milliseconds (see Table 3, below, for fitting results), indicating the existence of BET from $Mn^{2+}$.

TABLE 2

Nanosecond biexponential lifetime fitting results of exciton PL decay of DPA-MnQDs measured at different temperatures

| Sample Name | Temp. (° C.) | Amplitude ($N_{ns}$) | $f_1$* | $\tau_1$ (ns) | $\tau_2$ (ns) | Offset | Reduced $\chi^2$ |
|---|---|---|---|---|---|---|---|
| DPA-Mn08ZnS02 | 20 | (8.69 ± 0.04) × 10³ | 0.136 ± 0.003 | 0.83 ± 0.04 | 14.6 ± 0.1 | 20.6 ± 0.2 | 1.20 |
| | 29 | (7.40 ± 0.03) × 10³ | 0.134 ± 0.003 | 0.69 ± 0.04 | 13.7 ± 0.1 | 18.1 ± 0.2 | 1.22 |
| | 38 | (6.48 ± 0.03) × 10³ | 0.135 ± 0.003 | 0.69 ± 0.04 | 13.3 ± 0.1 | 16.1 ± 0.2 | 1.22 |
| | 48 | (5.67 ± 0.03) × 10³ | 0.144 ± 0.003 | 0.60 ± 0.04 | 12.3 ± 0.1 | 13.8 ± 0.2 | 1.18 |
| DPA-Mn08ZnS05 | 20 | (5.81 ± 0.03) × 10³ | 0.153 ± 0.004 | 0.84 ± 0.05 | 10.0 ± 0.1 | 35.1 ± 0.2 | 1.07 |
| | 29 | (4.75 ± 0.03) × 10³ | 0.160 ± 0.005 | 0.70 ± 0.05 | 8.37 ± 0.11 | 30.3 ± 0.2 | 1.12 |
| | 38 | (4.12 ± 0.03) × 10³ | 0.169 ± 0.005 | 0.80 ± 0.05 | 10.3 ± 0.2 | 27.2 ± 0.2 | 1.11 |
| | 48 | (3.48 ± 0.03) × 10³ | 0.177 ± 0.005 | 0.69 ± 0.05 | 8.92 ± 0.14 | 25.4 ± 0.2 | 0.97 |
| DPA-Mn08ZnS10 | 20 | (8.75 ± 0.03) × 10³ | 0.110 ± 0.003 | 0.67 ± 0.04 | 12.3 ± 0.1 | 23.9 ± 0.2 | 1.15 |
| | 29 | (8.42 ± 0.03) × 10³ | 0.106 ± 0.003 | 0.73 ± 0.05 | 12.9 ± 0.1 | 24.8 ± 0.2 | 1.19 |
| | 38 | (7.71 ± 0.03) × 10³ | 0.115 ± 0.003 | 0.79 ± 0.05 | 12.8 ± 0.1 | 26.2 ± 0.2 | 1.10 |
| | 48 | (7.46 ± 0.04) × 10³ | 0.122 ± 0.003 | 0.88 ± 0.05 | 14.0 ± 0.1 | 27.5 ± 0.2 | 1.16 |
| DPA-Mn02ZnS10 | 20 | (7.76 ± 0.03) × 10³ | 0.153 ± 0.003 | 0.66 ± 0.04 | 10.5 ± 0.1 | 8.55 ± 0.14 | 1.20 |
| | 29 | (8.21 ± 0.03) × 10³ | 0.147 ± 0.003 | 0.65 ± 0.04 | 9.87 ± 0.06 | 8.66 ± 0.14 | 1.33 |
| | 38 | (7.37 ± 0.03) × 10³ | 0.150 ± 0.003 | 0.66 ± 0.04 | 9.64 ± 0.07 | 9.17 ± 0.14 | 1.15 |
| | 48 | (8.23 ± 0.03) × 10³ | 0.158 ± 0.003 | 0.80 ± 0.04 | 10.5 ± 0.1 | 9.96 ± 0.14 | 1.24 |
| DPA-Mn05ZnS10 | 20 | (6.23 ± 0.01) × 10³ | 0.090 ± 0.001 | 2.02 ± 0.05 | 18.1 ± 0.1 | 77.7 ± 0.4 | 1.35 |
| | 29 | (5.65 ± 0.01) × 10³ | 0.093 ± 0.001 | 1.96 ± 0.05 | 18.3 ± 0.1 | 82.1 ± 0.4 | 1.22 |
| | 38 | (5.26 ± 0.01) × 10³ | 0.092 ± 0.001 | 1.91 ± 0.05 | 18.4 ± 0.1 | 88.4 ± 0.4 | 1.35 |
| | 48 | (4.78 ± 0.01) × 10³ | 0.093 ± 0.001 | 1.83 ± 0.05 | 17.4 ± 0.1 | 93.9 ± 0.4 | 1.36 |
| DPA-Mn17ZnS10 | 20 | (1.89 ± 0.02) × 10³ | 0.272 ± 0.008 | 0.44 ± 0.04 | 5.16 ± 0.11 | 8.81 ± 0.13 | 1.17 |
| | 29 | (1.62 ± 0.02) × 10³ | 0.299 ± 0.008 | 0.49 ± 0.04 | 6.85 ± 0.17 | 9.52 ± 0.13 | 1.08 |
| | 38 | (1.50 ± 0.02) × 10³ | 0.313 ± 0.009 | 0.55 ± 0.04 | 7.1 ± 0.10 | 11.0 ± 0.1 | 1.02 |
| | 48 | (1.31 ± 0.02) × 10³ | 0.333 ± 0.010 | 0.57 ± 0.04 | 6.58 ± 0.22 | 11.7 ± 0.1 | 1.12 |

*$f_1$ is the fraction of the short lifetime ($\tau_1$) component.

spectra of DPA-Mn08ZnS10 as a function of temperature. The relative intensity of exciton emission is seen to increase with temperature. This is attributed to increased contribution of BET at higher temperatures. The isosbestic point of these two emissions is at 565 nm, which serves as the separating wavelength for the ratiometric measurements. It is important to note that in practical applications, the ratiometric temperature sensing data can be obtained by simply using a dichroic filter set to the isosbestic point and two photodiode detectors—one for the exciton emission and one for the $Mn^{2+}$ emission. With this measurement technique, one does not have to rely on a spectrometer and curve fitting computations, implying robust and faster measurements.

Further insights can be obtained from photoluminescence lifetime measurements. The nanosecond lifetime data can be suitably modeled by two exponential decays with a constant intensity offset, and the fitting results are tabulated in Table 2, below (see example 11). The fast decay (~1 ns) is assigned to either the exciton non-radiative relaxation and/or the energy transfer from exciton to $Mn^{2+}$ excited states. The second, slower decay (~13 ns) is commensurate with the

TABLE 3

Millisecond stretched exponential lifetime fitting results of exciton PL decay of DPA-MnQDs

| Sample Name | $\tau_{KWW}$ (ms) | β | <Lifetime> | Reduced $\chi^2$ |
|---|---|---|---|---|
| DPA-Mn08ZnS02 | 0.045 | 0.392 | 0.906 | 1.83 |
| DPA-Mn08ZnS05 | 0.106 | 0.423 | 1.40 | 1.47 |
| DPA-Mn08ZnS10 | 0.210 | 0.453 | 1.98 | 1.62 |
| DPA-Mn02ZnS10 | 0.161 | 0.422 | 2.16 | 1.5 |
| DPA-Mn05ZnS10 | 0.243 | 0.445 | 2.48 | 1.99 |
| DPA-Mn17ZnS10 | 0.342 | 0.508 | 1.93 | 1.38 |

Uncertainties were not included in this table because they are less than 0.5% of the fitted values.

To quantify the ratiometric temperature sensitivity in DPA-MnQDs with different shell thicknesses, the exciton emission ratios ($PL_{exc}/PL_{total}$) at different temperatures were measured. As mentioned above, the $PL_{exc}/PL_{total}$ ratio is obtained from the ratio of the integrated PL intensity between 415 and 565 nm to its total PL intensity. The temperature sensitivity of DPA-MnQDs is represented by the slope of $PL_{exc}/PL_{total}$ as a function of temperature, shown in FIG. 3C. They are (2.6±0.3)×10⁻³, (4.0±0.4)×10⁻³, and $(3.0\pm0.3)\times10^{-3}$° C.-1 for DPA-Mn08ZnS02, DPA-Mn08ZnS05, and DPA-Mn08ZnS10, respectively.

The non-radiative relaxation rate of the excitonic state tends to increase at higher temperatures, resulting in reduced emission intensity. The contribution of the temperature-dependent nonradiative relaxation channel can be examined by plotting the total intensity $PL_{total}$ as a function of temperature, shown in FIG. 3D. It is evident that the DPA-Mn08ZnS02 construct exhibits significant temperature-dependent PL intensity reduction; therefore, the slope shown in FIG. 3C for this construct is primarily driven by the reduction of the total intensity, rather than by the relative populations of the $Mn^{2+}$ and the excitonic states. This argument was supported by the lifetime trace of DPA-Mn08ZnS02, which does not show temperature-dependent intensity plateau as expected from BET (quantitative values are tabulated in the Table 2). In other words, the major contribution of temperature-dependent $PL_{exc}/PL_{total}$ in DPA-Mn08ZnS02 is from the temperature-dependent ratio of non-radiative transition of exciton and $Mn^{2+}$ emission. Therefore, the apparent $PL_{exc}/PL_{total}$ ratio is due to the combined effect of the temperature dependent BET and non-radiative relaxation of exciton and $Mn^{2+}$ emission. The DPA-Mn08ZnS05 construct shows the highest temperature sensitivity among the three studied (FIG. 3C) with moderate temperature-dependent $PL_{total}$ intensity decrease (FIG. 3D), suggesting a combined effect of BET and non-radiative transitions. In the subsequent studies, the MnQDs with thick ZnS shell (ZnS=10.4 MLs) are used to examine the effect of $Mn^{2+}$ concentration because the total PL intensity is the least sensitive (only about 6%) to temperature changes (FIG. 3D).

Example 3—Tuning MnQDs by Increasing $Mn^{2+}$ Dopant Concentration

Figure 4:
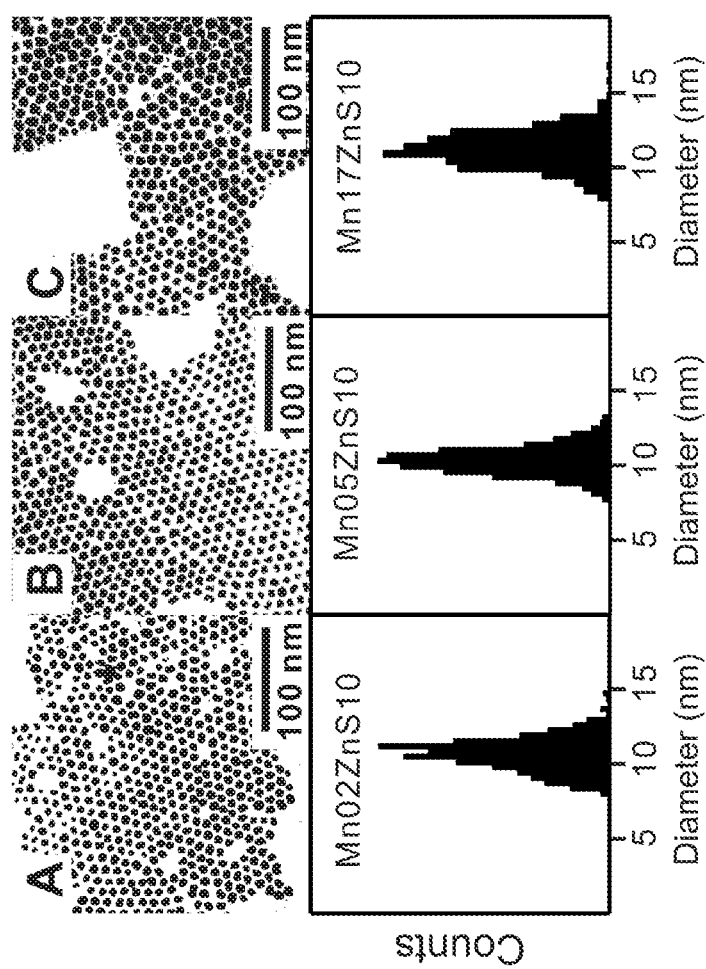
FIGS. 4A-C illustrate representative TEM images of Mn02ZnS10 (A), Mn05ZnS10 (B), and Mn17ZnS10 (C). The bottom panel shows size distribution histograms of $Mn^{2+}$-doped quantum dots from TEM data. The average diameters of Mn02ZnS10, Mn05ZnS10, and Mn17ZnS10 are 10.7, 10.3, and 11.1 nm, respectively.

To investigate the effect of $Mn^{2+}$ dopant content, a series of samples with the nominal number of $Mn^{2+}$ ion per quantum dot at 2, 5, 8, and 17, designated as DPA-Mn02ZnS10, DPA-Mn05ZnS10, DPA-Mn08ZnS10, and DPA-Mn17ZnS10, respectively, were prepared. TEM images of the MnQDs with different Mn/QD are shown in FIGS. 4A-C and the ICP-MS data of the MnQDs via Route A are shown in Table 4, below.

TABLE 4

| | ICP-MS data | | |
|---|---|---|---|
| Sample name | Cd (atomic %) | Mn (atomic %) | Zn (atomic %) |
| Mn02ZnS10 | 6.8 | 0.02 | 93 |
| Mn05ZnS10 | 5.4 | 0.04 | 95 |
| Mn08ZnS10 | 6.4 | 0.08 | 93 |
| Mn17ZnS10 | 4.7 | 0.12 | 95 |

The Mn/QD dependent photoluminescence spectra of DPA-MnQDs at 20° C. are displayed in FIG. 5B. With increasing $Mn^{2+}$ concentration, the relative exciton emission intensity decreases, suggesting that the $Mn^{2+}$ sites deplete energy from the excitonic state. The shifts in the $Mn^{2+}$ emission peak position of DPA-MnQDs are likely caused by batch-to-batch variations. Following the earlier studies, the red-shifts of exciton emission with increasing $Mn^{2+}$ concentration can be attributed to the exchange interaction between the $Mn^{2+}$ ion and the band electrons. The temperature-dependent $PL_{exc}/PL_{total}$ for this series of DPA-MnQDs are displayed in FIG. 5C, exhibiting slopes of $(1.7\pm0.3)\times10^{-3}$, $(3.1\pm0.1)\times10^{-3}$, $(3.0\pm0.3)\times10^{-3}$, and $(3.0\pm0.1)\times10^{-3}$° C.-1, for Mn/QD=2, 5, 8, and 17, respectively. The temperature sensitivity (slope) of DPA-Mn02ZnS10 appears to be significantly lower than that of other samples, likely due to fewer $Mn^{2+}$ sites available for energy storage and consequently lowering the contribution from BET. Conversely, DPA-MnQDs with higher $Mn^{2+}$ concentrations (5 Mn/QD and above) exhibit similar temperature sensitivities. This result suggests that high $Mn^{2+}$ concentration is optimal for good temperature sensitivity. It also implies that potential dot-to-dot variations in $Mn^{2+}$ concentration may be alleviated for temperature measurement applications with a larger Mn/QD ratio.

Insights about the relative excitonic populations due to BET from the $Mn^{2+}$ dopant can be obtained from photoluminescence lifetime measurements. As before, the exciton decay lifetimes of DPA-MnQDs with lower $Mn^{2+}$ concentrations (Mn/QD at 2, 5, 8) are similar (11~18 ns), shown in Table 2. In temperature-dependent lifetime traces of DPA-Mn17ZnS10, the plateau intensities are seen to increase with temperature, indicating a greater BET contribution with higher temperatures.

Assuming that the ~10-ns exciton decay exclusively comes from undoped DPA-MnQDs, a method was developed to estimate the extent of undoped dots in the samples based on the lifetime traces (see example 11). The estimated amounts of undoped dots were 15%, 14%, 6.8%, and 3.4% for Mn/QD=2, 5, 8, and 17, respectively. It should be pointed out that quencher-decorated quantum dots could exhibit excursions to high-emission and long-lifetime states on the single-particle level, as has been nicely demonstrated by Song et al., 2011, ACS Nano, 128, 13320-21, which is incorporated herein by reference as if fully set forth. Therefore, the estimation assuming the ~10-ns component comes exclusively from undoped quantum dots is an upper bound for the percentage of undoped DPA-MnQDs. In addition, assuming the distribution of $Mn^{2+}$ in the samples follows the Poisson statistics, the amount of undoped dots were estimated to be 14%, 0.67%, 0.03%, and 0% for Mn/QD=2, 5, 8, and 17, respectively. This result is consistent with the PL spectrum of Mn17ZnS10 measured at low temperature (ca. −50° C.), where exciton emission was not observed. Furthermore, the temperature sensitivities (slopes) of DPA-MnQDs with high $Mn^{2+}$ concentration (Mn/QD≥5) are almost the same, implying the contribution of undoped dots on temperature sensing in the DPA-MnQDs with high $Mn^{2+}$ concentrations (Mn/QD≥5) are negligible.

To further characterize the sensitivity of DPA-MnQDs, the precision of the temperature sensing, i.e., the extent of temperature-dependent uncertainties, was estimated from the error bars in the temperature-dependent $PL_{exc}/PL_{total}$ plots, shown in Table 1. Low precision (~2.2° C.) was obtained from the DPA-MnQDs with thin ZnS shell (DPA-Mn08ZnS02) and low $Mn^{2+}$ dopant concentration (DPA-Mn02ZnS10). The precision of the DPA-MnQDs with thick ZnS shell and high $Mn^{2+}$ dopant concentration was relatively high, ≥0.59° C. (in DPA-Mn05ZnS10), comparable to the precision of the previously reported MnQDs in toluene (Vlaskin et al., 2010, Nano Lett., 10, 3670-74, which is incorporated herein by reference as if fully set forth). These results support that thick ZnS shell and high $Mn^{2+}$ dopant concentration are two key parameters to maintain excellent temperature sensitivity in aqueous solutions.

Materials. All chemicals were used without further purification. Diphenylphosphine (98%), manganese(II) acetate (98%), sulfur (99.998%), cadmium oxide (CdO, ≥99.99%), olelylamine (OAm, Tech grade), oleic acid (Tech 90%), anhydrous toluene (99.8%) and D-penicillamine (DPA, 98-101%) were purchased from Sigma-Aldrich. 1-octadecene (ODE, 90% Tech) and cadmium acetate dehydrate (98%) were purchased from Acros organics. Selenium shots (99.999+%) and zinc stearate (Cat. No 33238) were purchased from Alfa Aesar.

Example 4—Preparation of Diphenylphosphine Selinide (DPPSe)

DPPSe was prepared by following previously published procedures (Evans et al., 2010, J. Am. Chem. Soc., 132, 10973-75, which is incorporated herein by reference as if fully set forth). A mixture of selenium shot (1.5 g, 20 mmol) and diphenylphosphine (3.48 mL, 20 mmol) was dissolved in 25 mL of anhydrous toluene in a three-neck flask under $N_2$ environment. The mixture was refluxed for 16 hours, forming a clear and slightly yellow solution. Toluene was removed under reduced pressure, and the resulting white solid powder (DPPSe) was collected and stored. Note that diphenylphosphine (DPP) is a pyrophoric chemical. To perform the synthesis of DPPSe without using a glovebox, it is necessary to purchase DPP (252964-50G, Sigma-Aldrich) and anhydrous toluene (244511-100ML, Sigma-Aldrich) stored in septum-sealed bottles. DPP and anhydrous toluene were transferred using syringes into the flask containing selenium after proper degassing and subsequent placement in nitrogen environment at room temperature. After the reaction, the air-stable DPPSe is formed. A large quantity of DPPSe can be prepared, so the synthesis of DPPSe does not need to be performed very often.

Example 5—Synthesis of CdSSe Nanocrystals Using DPPSe (Route A)

The synthetic procedure was modified from a previously published procedure (Chen et al., 2010, J. Phys. Chem. C, 114, 4418-23, which is incorporated herein by reference as if fully set forth). Colloidal CdSSe nanocrystals were prepared by injecting sulfur-selenium (S—Se) precursor into a hot cadmium (Cd) precursor solution. The S—Se stock solution (molar ratio 60:40) was freshly prepared using 38.4 mg of sulfur, 212.0 mg of DPPSe and 8 mL of ODE in a three-neck 50-mL flask (aged S—Se stock solution may cause the first absorption and emission peaks of the CdSSe core to blue shift, indicating a decrease of Se content in the nanocrystals). The solution was degassed, refilled with nitrogen and heated to 120° C., producing a yellow solution. In a separate three-neck flask, a Cd precursor stock solution was prepared using 128 mg of CdO, 2.4 mL of oleic acid and 8 mL of ODE. The solution was degassed, refilled with nitrogen and heated to 280° C., producing a clear solution. 2 mL of S—Se stock solution was injected into the Cd precursor solution, lowering the temperature to 265° C. After injection, the mixture turned orange, indicating the formation of CdSSe nanocrystals. The temperature was kept at 265° C. for about 8 minutes for further nanocrystal growth. The reaction was quenched by removing the heat source, and the resulting solution was cooled to room temperature. Unreacted precursors and excess surfactants were removed by performing the following washing procedure. The resulting nanocrystals were precipitated by adding acetone. A pellet of nanocrystals was formed after centrifugation at 4,000 rpm for 10 minutes. The supernatant was discarded, and the yellow pellet containing CdSSe was re-suspended in 10 mL of toluene. 10 mL of methanol was added, forming a turbid solution, and the mixture was centrifuged at 4,000 rpm for 5 minutes. The supernatant was discarded, and the yellow precipitate was re-suspended in 7 mL of hexane. The nanocrystals were centrifuged again for 5 min at 4,000 rpm to remove undesirable large particles, and the yellow transparent solution was filtered through a 0.2 μm Polytetrafluoroethylene (PTFE) filter (Fisherbrand, 09-719G) into an amber vial. The resultant CdSSe cores were stored at 4° C.

Example 6—Synthesis of CdSSe Nanocrystals Using Se Powder (Route B)

The nanocrystals were prepared according to previously published noninjection procedures with minor modifications (Zou et al., 2010, Nanoscale Res. Lett., 5, 966-71; Ouyang et al., 2009, J. Phys. Chem. C, 113, 5193-5200, which are incorporated herein by reference as if fully set forth). For 40% Se nanocrystals, 1 mmol of cadmium acetate dihydrate, 15 mL ODE and 2.4 mL of oleic acid were heated at 120° C. for 30 minutes under vacuum. The resulting clear solution was cooled under $N_2$ flow to 30° C. and added to a dry mixture of 0.2 mmol of Se and 0.3 mmol of S degassed in a three-neck round bottom flask. The reaction mixture was raised to 240° C. under $N_2$ environment at a rate of 10° C. per minute. When the reaction reached 240° C., the reaction time began. Nanocrystals were allowed to grow for 3 minutes after which the reaction was quenched by injecting 8 mL of ambient temperature ODE. The product was cooled to room temperature by removing the heat source. The washing step followed the same procedure described in example 5 above.

Example 7—Preparation of Zinc, Sulfur, and Manganese Precursor Solutions for $Mn^{2+}$-Doped QDs A 0.04 M zinc stearate $(Zn(St)_2)$ stock solution was prepared using 1.01 g of $Zn(St)_2$, 1 mL of oleic acid, and 39 mL of ODE. The solution was degassed, refilled with nitrogen and kept at room temperature. 0.04 M sulfur stock solution was prepared using 51.2 mg of sulfur and 40 mL of ODE. The solution was degassed, refilled with nitrogen and heated to 120° C. The resulting clear solution was cooled to 60° C. 7.25 mM manganese precursor solution was prepared using 10.4 mg of $Mn(OAc)_2$. After the powder was degassed at room temperature for 10 minutes, 8 mL of oleylamine was injected into the flask. After an additional 10 minutes, the resulting clear, pale yellow solution was refilled with nitrogen and kept at room temperature. The Mn precursor solution needs to be prepared immediately prior to use to avoid oxidation. Oxidation of Mn precursor can be easily observed by the color change from clear to brown.

Example 8—Synthesis of $Mn^{2+}$-Doped QDs from CdSSe Cores $Mn^{2+}$-doped QDs were prepared by following previously published procedures (Yang et al., 2006, J. Am. Chem. Soc., 128, 12428-29; Yang et al., 2008, J. Am. Chem. Soc., 130, 15649-61, which are incorporated herein by reference as if fully set forth) with modifications. In the published procedures, $Mn^{2+}$-doped QDs were prepared by three separated steps—the initial ZnS shell coating, Mn cation doping, and the final ZnS shell coating. To simplify the synthetic procedure, the three separated steps were combined. First, CdSSe nanocrystal cores (~$6\times10^{-8}$ mol) were placed in a three-neck flask with 2 mL of oleylamine and 6 mL of ODE. The mixture was degassed to remove hexane, refilled with nitrogen and heated to 120° C. ZnS shell coating was performed following the SILAR procedure (Li et al., 2003, J. Am. Chem. Soc., 125, 12567-75, which is incorporated herein by reference as if fully set forth), where approximately 0.8 monolayer (ML) of ZnS shell was grown in every cycle. 0.52 mL of 0.04-M sulfur stock solution was added drop-wise into the mixture and heated to 220° C. for 10 minutes. 0.52 mL of 0.04-M $Zn(St)_2$ stock solution was added drop-wise into the mixture, and kept at 220° C. for another 10 minutes, forming 0.8 ML of ZnS shell. Another 0.8 ML of ZnS was coated by drop-wise addition of 0.64-mL sulfur stock solution and 0.64-mL $Zn(St)_2$ stock solution at 220° C. where each sulfur or Zn addition was metered over 10 minutes. After heating the mixture to 280° C., 0.90 mL of 0.04-M sulfur stock solution and 0.79 mL of 7.25-mM Mn stock solution were added drop-wise, and the mixture was kept at 280° C. for 20 minutes. Note that the Mn-growth (measured/added) yield is ~11% according to the inductively coupled plasma mass spectroscopy (ICP-MS) data measured by Evans Analytical Group. 0.79 mL of 0.04-M Zn stock solution was added at 280° C., and the mixture was kept at 280° C. for 10 min. After doping the quantum dot with Mn, the subsequent ZnS shell coating was performed by growing 0.8 ML of ZnS sequentially at 280° C. until the desired thickness of ZnS shell was obtained. The product was cooled down to room temperature by removing the heat source. The washing step followed the same procedure described for the CdSSe cores in example 5. 10.4 MLs of external ZnS layers of MnQDs were achieved by coating additional 5.6 MLs of ZnS shell on the MnQDs with 4.8 MLs of ZnS shell after washing.

Example 9—DPA Passivation Procedure

The DPA passivation procedure was modified based on previous procedures (Breus et al., 2009, ACS Nano, 3, 2573-80; Moloney et al., 2007, Chem. Commun., 3900-02, which are incorporated herein by reference as if fully set forth), primarily through the use of sonication to accelerate the passivation process. Briefly, water-soluble passivation was conducted by sonicating 10 nmol of $Mn^{2+}$-doped QDs suspended in 400-μL 0.8-M NaOH/methanol solution with D-penicillamine (100 mg/mL) and 900 μL of chloroform for one hour. Biphasic exchange was performed by addition of 0.1-mL 1×PBS and additional sonication for 20 minutes. To retrieve the water-soluble MnQDs, the top aqueous layer was collected, treated with ethanol, followed by centrifugation at 4000 rpm for 10 minutes. The precipitated DPA-coated $Mn^{2+}$-QDs (DPA-MnQDs) were then re-dispersed in 1×PBS (pH=7.4) buffer. The DPA-MnQDs were annealed to provide better stability in water-based solvents for photoluminescence and lifetime measurements.

Example 10—Photoluminescence Quantum Yield Measurements

The photoluminescence quantum yields of DPA-MnQDs were estimated from the integrated PL intensity ratio of DPA-MnQDs to a reference dye, quinine in 0.1-M $H_2SO_4$, the quantum yield of which is reported to be ~55%. The measurements were performed at 20° C., and the excitation wavelength was 350 nm with 1-nm excitation width.

Example 11—Photoluminescence and Lifetime Measurements

Photoluminescence measurements were performed using the Flurolog-3 fluorometer (Horiba Jobin-Yvon). Exciton lifetime measurements were performed using the Time-Correlated Single Photon Counting (TCSPC) option of the fluorometer where the QDs were excited by a NanoLED device. The excitation wavelength was 445 nm with pulse duration of about 1.2 ns. The detection wavelength was set to the peak position of exciton emission with a spectral window of 10 nm. The fluorescence lifetime window was set to a time range of 200 ns. The PL lifetimes on microsecond and millisecond timescale were obtained using the Multi-Channel Scaler (MCS) option of the fluorometer where the MnQDs were excited by SpectraLED device (excitation wavelength was 390 nm). The detection wavelengths were set to 510 nm for exciton emission and 620 nm for $Mn^{2+}$ emission with a spectral window of 15 nm. The lifetime window was set to a time range of 80 ms with a time resolution of 20 μs. The dark counts of PL lifetime traces on microsecond and millisecond timescale were subtracted before the performance of curve fitting.

Analysis of photoluminescence lifetime. The nanosecond PL lifetime decays at the 510-nm exciton emission were fitted to a biexponential model, $$g_{ns}(t) = N_{ns}\left[\frac{f_1}{\tau_1}e^{-t/\tau_1} + \frac{1-f_1}{\tau_2}e^{-t/\tau_2}\right]\delta t + B_{ns} + g_{offset} \quad \text{Equation 1}$$

where $N_{ns}$ is the number of photons from the nanosecond decay channels, $f_1$ the fraction of the faster decay channel ($\tau_1$<1 ns), $\delta t$ the TCSPC digitization time ($\delta t$=0.2237 ns in the present case), B the background count of the fluorometer measured from a separate control experiment, and $g_{offset}$ the signal offset resulting from the back energy transfer from the coupling $Mn^{2+}$ ions. Eq. (1) was convolved with an instrument response function and compared with the PL lifetime. The optimal $N_{ns}$, $f_1$, $\tau_1$, $\tau_2$, and $g_{offset}$ were located through a $\chi^2$ minimization procedure.

The millisecond PL lifetime decays were fitted to a stretched exponential (Kohlrausch-Williams-Watts) model, $$g_{ns}(t) = N_{ns}\frac{1}{\tau_{KWW}\Gamma[1+\beta_{KWW}^{-1}]}\exp\left[-\left(\frac{t}{\tau_{KWW}}\right)^{\beta_{KWW}}\right]\delta t + B_{ms} \equiv \quad \text{Equation 2}$$

$$N_{ms}g_{KWW}(t) + B_{ms}$$

where $N_{ms}$ is the number of photons from the millisecond decay channels, $\tau_{KWW}$ and $\beta_{KWW}$ are parameters for the stretched exponential, $\delta t$ the TCSPC digitization time ($\delta t$=20 μs in the present case), and $B_{ms}$ is the background. The parameters $N_{ms}$, $\tau_{KWW}$ and $\beta_{KWW}$ were optimized through a $\chi^2$ minimization procedure after convolving Eq. (2) with an instrument response function on this timescale. The expectation value for the millisecond lifetime was calculated using the optimized parameters with the formula, $$\langle\tau\rangle_{KWW} =$$

$$\int_0^\infty \frac{t}{\tau_{KWW}\Gamma[1+\beta_{KWW}^{-1}]}\exp\left[-\left(\frac{t}{\tau_{KWW}}\right)^{\beta_{KWW}}\right]dt = \frac{\tau_{KWW}\Gamma[1+2\beta_{KWW}^{-1}]}{2\Gamma[1+\beta_{KWW}^{-1}]}.$$

Error bars for the PL decay parameters were calculated using the analytical covariance matrices derived from Eqs. (1) and (2). Unless specified, all data analyses were carried out using Matlab (Mathworks, version 2011a).

Estimation of undoped MnQD percentage. The probability for a photon from the millisecond decay channel to appear in the nanosecond window is expected to be diminishingly small. However, if the relative population through the millisecond channel is great, as in the present case, it will become detectable in the nanosecond time window. That is, the ~ms decay from the BET contribution to the exciton radiative relaxation on the nanosecond time window would appear as a constant offset, denoted as $g_{offset}$ in Eq. (1). Once the parameters of the millisecond decay were determined, Eq. (2), the probability for one photon from the millisecond channel to appear in the nanosecond window can be calculated by $$g_{ns \leftarrow ms} \approx \Sigma_{k=0}^{\infty} g_{KWW}(kT)$$

where T is the period between consecutive laser excitation pulses. The summation takes into account the situation when the stop signal (the laser pulse immediately following the excitation pulse) arrives before the millisecond PL decay has completed in a TCSPC setup. In the present case, T=1 μs for the nanosecond PL lifetime measurements and the summation was calculated numerically. At the exciton emission wavelength, the number of photons coming from undoped and doped MnQDs are $$N_{undoped} = N_{ns}(1-f_1) \text{ and } N_{doped} = g_{offset}/g_{ns \leftarrow ms},$$

respectively. The percentage of undoped MnQDs in a sample is therefore, $$P_{undoped} = N_{undoped}/(N_{undoped} + N_{doped})$$

Temperature-dependent photoluminescence measurements. The excitation wavelength was set to 400 nm with 1-nm excitation width. The temperature-dependent measurements were conducted using a cuvette holder to hold the sample while water was pumped around the holder from an external circulating temperature bath. The temperature was measured by inserting a thermocouple probe through a septum-capped cuvette. The temperature-dependent PL spectra were collected from DPA-MnQDs in PBS buffer solution.

Example 12—Transmission Electron Microscopy (TEM)

TEM images were collected using the Philips CM100 TEM. The sample was prepared by adding a drop of diluted MnQDs in hexane solution on a carbon-supported copper grid. The TEM images were analyzed using the image processing toolbox in the Matlab. The TEM images were converted into black-and-white images. In order to ensure the black-white images well present the nanocrystals in the original TEM images, it is necessary to fine-tune the threshold for the image conversion. In the black-and-white binary image, the connected pixels were considered as nanocrystals. The diameters of nanocrystals were estimated from the area of the connected components, assuming all the particles are circular on two-dimensional projection of TEM. In general, the average diameters were obtained from more than 500 particles, which are consistent with the hand-measured values (100 particles).

The references cited throughout this application are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. An $Mn^{2+}$-doped quantum dot comprising:
   a fluorescent semiconductor core comprising CdSSe;
   an initial shell covering the fluorescent semiconductor core, wherein the initial shell is an initial ZnS shell, an initial CdS shell, or an initial ZnSe shell;
   an $Mn^{2+}$ dopant associated with the initial shell; and
   a protection shell covering the initial shell and the $Mn^{2+}$ dopant, wherein the protection shell is a ZnSe protection shell or a $Zn_{1-x}Cd_xS$ protection shell, wherein X is the ratio of Cd/(Cd+Zn) in the $Zn_{1-x}Cd_xS$ protection shell and has a value from 0 to 0.5.

2. The $Mn^{2+}$-doped quantum dot of claim 1 further comprising a passivating agent associated with the protection shell.

3. The $Mn^{2+}$-doped quantum dot of claim 2, wherein the passivating agent is D-penicillamine.

4. The $Mn^{2+}$-doped quantum dot of claim 2, wherein the passivating agent is cystine.

5. The $Mn^{2+}$-doped quantum dot of claim 2, wherein the passivating agent is selected from the group consisting of dihydrolipoic acid, dihydrolipoic acid derivatives, a polyethylene glycol functionalized dihydrolipoic acid, and an —SH group functionalized passivating agent.

6. A method of labeling a biological specimen comprising:
   contacting the biological specimen with the $Mn^{2+}$-doped quantum dot of claim 1.

7. The method of claim 6, wherein the biological specimen is a tissue, a cell, an intracellular organelle, an individual protein or a cellular component.

8. An $Mn^{2+}$-doped quantum dot comprising:
   A fluorescent semiconductor core comprising a substance selected from the group consisting of copper indium sulfide, zinc indium copper sulfide, indium phosphide, and CdSSe;
   an initial shell covering the fluorescent semiconductor core, wherein the initial shell is an initial ZnS shell, an initial CdS shell, or an initial ZnSe shell;
   an $Mn^{2+}$ dopant associated with the initial shell;
   a protective shell covering the initial shell and the $Mn^{2+}$ dopant, wherein the productive shell is a ZnSe protective shell or a $Zn_{1-x}Cd_xS$ protective shell where X is the ratio of Cd/(Cd+Zn) in the $Zn_{1-x}Cd_xS$ protective shell and has a value from 0 to 0.5 and
   a passivating agent associated with the protective shell selected from D-penicillamine or cysteine.

9. The $Mn^{2+}$-doped quantum dot of claim 8, wherein the fluorescent semiconductor core includes CdSSe.

10. The $Mn^{2+}$-doped quantum dot of claim 8, wherein the passivating agent is D-penicillamine.

11. The $Mn^{2+}$-doped quantum dot of claim 8, wherein the passivating agent is cystine.

12. The $Mn^{2+}$-doped quantum dot of claim 8, wherein the protection shell is a ZnS protection shell, which is the $Zn_{1-x}Cd_xS$ protection shell when x is zero.

13. The $Mn^{2+}$-doped quantum dot of claim 8, wherein the protection shell is the ZnSe protection shell.

14. The $Mn^{2+}$-doped quantum dot of claim 8, wherein the protection shell is the $Zn_{1-x}Cd_xS$ protection shell.

15. The $Mn^{2+}$-doped quantum dot of claim 1, wherein the protection shell is a ZnS protection shell, which is the $Zn_{1-x}Cd_xS$ protection shell when x is zero.

16. The $Mn^{2+}$-doped quantum dot of claim 1, wherein the protection shell is the ZnSe protection shell.

17. The $Mn^{2+}$-doped quantum dot of claim 1, wherein the protection shell is the $Zn_{1-x}Cd_xS$ protection shell.

* * * * *